US008232094B2

(12) United States Patent
Hasson et al.

(10) Patent No.: US 8,232,094 B2
(45) Date of Patent: Jul. 31, 2012

(54) REAL-TIME PCR IN MICRO-CHANNELS

(75) Inventors: Kenton C. Hasson, Germantown, MD (US); Gregory A. Dale, Gaithersburg, MD (US); Hiroshi Inoue, Bethesda, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 142 days.

(21) Appl. No.: 12/578,194

(22) Filed: Oct. 13, 2009

(65) Prior Publication Data

US 2010/0028980 A1 Feb. 4, 2010

Related U.S. Application Data

(62) Division of application No. 11/505,358, filed on Aug. 17, 2006, now Pat. No. 7,629,124.

(60) Provisional application No. 60/806,440, filed on Jun. 30, 2006.

(51) Int. Cl.
*C12M 3/00* (2006.01)
*C12M 1/34* (2006.01)
(52) U.S. Cl. .................. 435/286.5; 435/287.2
(58) Field of Classification Search .............. None
See application file for complete search history.

(56) References Cited

U.S. PATENT DOCUMENTS

| 6,033,880 | A | 3/2000 | Haff et al. |
| 6,174,670 | B1 | 1/2001 | Wittwer et al. |
| 6,232,079 | B1 | 5/2001 | Wittwer et al. |
| 6,303,343 | B1 | 10/2001 | Kopf-Sill |
| 6,387,621 | B1 | 5/2002 | Wittwer |
| 6,960,437 | B2 | 11/2005 | Enzelberger et al. |
| 7,015,030 | B1 | 3/2006 | Fouillet et al. |
| 2004/0132080 | A1 | 7/2004 | Kawaguchi et al. |
| 2004/0180346 | A1 | 9/2004 | Anderson et al. |
| 2004/0224325 | A1 | 11/2004 | Knapp et al. |
| 2004/0234966 | A1 | 11/2004 | Bryning et al. |
| 2005/0042639 | A1 | 2/2005 | Knapp et al. |
| 2005/0075683 | A1 | 4/2005 | Miesel et al. |
| 2005/0202489 | A1 | 9/2005 | Cho et al. |
| 2005/0274617 | A1 | 12/2005 | Bryning |

FOREIGN PATENT DOCUMENTS

WO  2005075683 A1  8/2005

OTHER PUBLICATIONS

Lagally et al., "Single-Molecule DNA Amplification and Analysis in an Integrated Microfluidic Device," Analytical Chemistry, vol. 73, No. 3, (2001) pp. 565-570.
Kopp et al., "Chemical Amplification: Continuous-Flow PCR on a Chip," Science, vol. 280, (1998) pp. 1046-1048.
Dorak, "Real-Time PCR," http://dorakmt.tripod.com/genetics/realtime.html Feb. 21, 2006.
Meldrum, "Automation for Genomics, Part Two: Sequencers, Microarrays, and Future Trends," Genome Research, vol. 10, (2000) pp. 1288-1303.
Park, et al., "Cylindrical compact thermal-cycling device for continuous-flow polymerase chain reaction," Anal. Chem., vol. 75, No. 21 (2003) pp. 6029-6033.
Meldrum, "Automation for Genomics, Part One: Preparation for Sequencing," Genome Research, vol. 10, (2000) pp. 1081-1092.

*Primary Examiner* — Kenneth R. Horlick
*Assistant Examiner* — David Thomas
(74) *Attorney, Agent, or Firm* — Rothwell, Figg, Ernst & Manbeck, P.C.

(57) ABSTRACT

The present invention relates to methods for amplifying nucleic acids in micro-channels. More specifically, the present invention relates to methods for performing a real-time polymerase chain reaction (PCR) in a continuous-flow microfluidic system and to methods for monitoring real-time PCR in such systems.

15 Claims, 12 Drawing Sheets

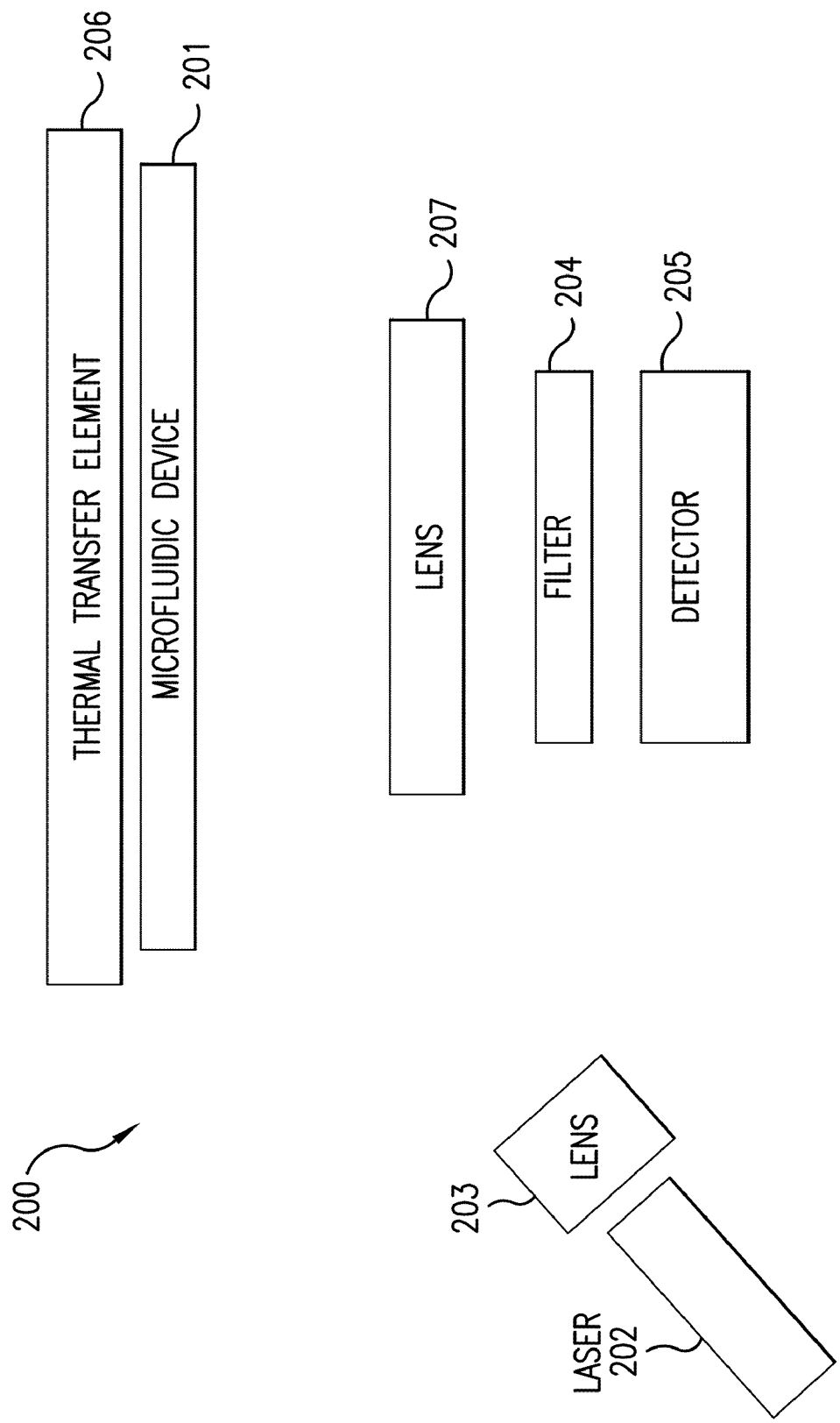

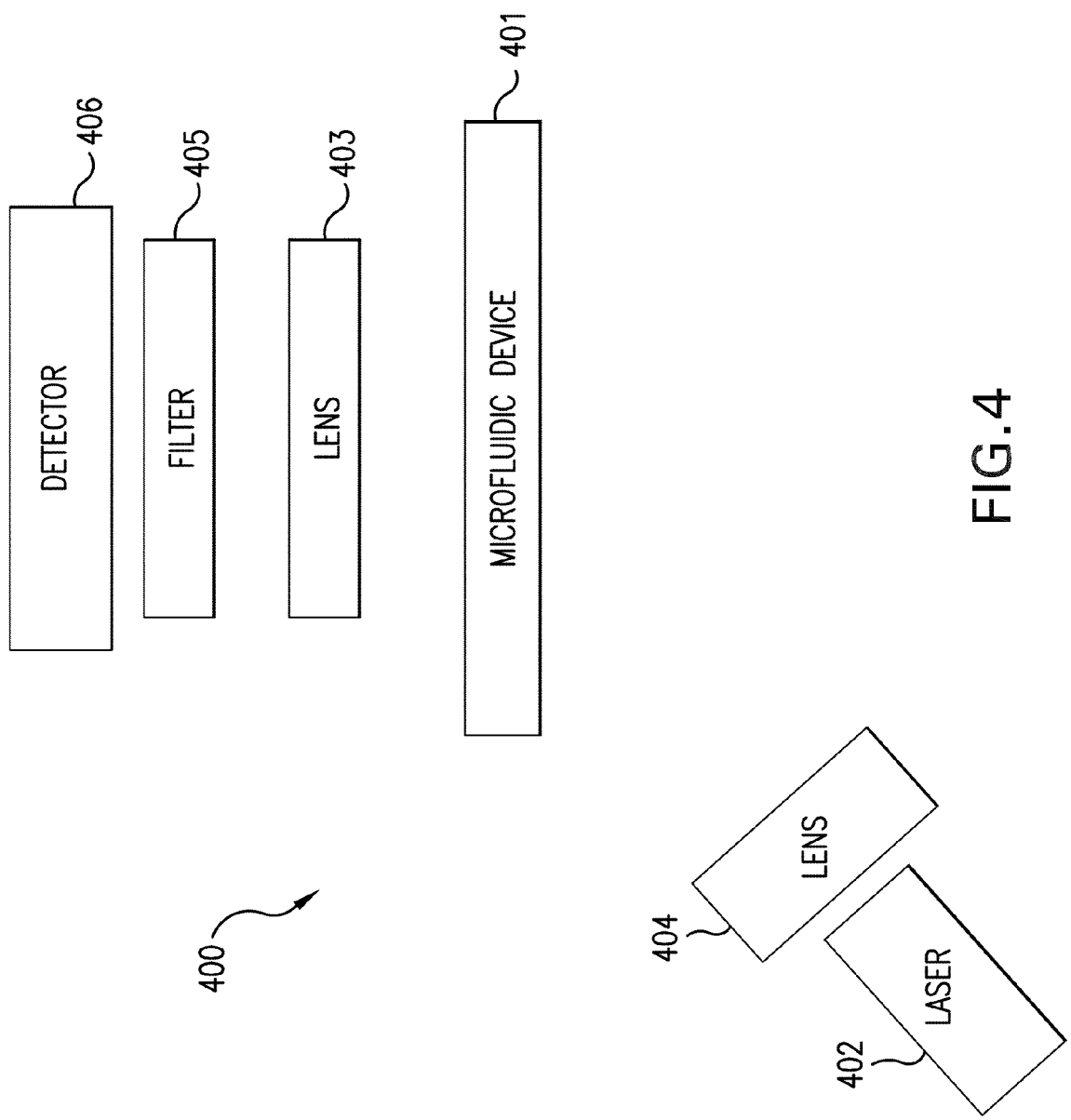

REAL-TIME PCR IN MICRO-CHANNELS

CROSS-REFERENCE TO RELATED APPLICATION

The present application is a divisional of U.S. patent application Ser. No. 11/505,358, filed Aug. 17, 2006, which claims priority to U.S. provisional patent application Ser. No. 60/806,440 filed, Jun. 30, 2006, which is incorporated herein by reference in its entirety.

BACKGROUND OF THE INVENTION

1. Field of the Invention

The present invention relates to methods for amplifying nucleic acids in micro-channels. More specifically, the present invention relates to methods for performing a real-time polymerase chain reaction (PCR) in a continuous-flow microfluidic system and to methods for monitoring real-time PCR in such systems.

2. Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

Several different real-time detection chemistries now exist to indicate the presence of amplified DNA. Most of these depend upon fluorescence indicators that change properties as a result of the PCR process. Among these detection chemistries are DNA binding dyes (such as SYBR® Green) that increase fluorescence efficiency upon binding to double stranded DNA. Other real-time detection chemistries utilize Foerster resonance energy transfer (FRET), a phenomenon by which the fluorescence efficiency of a dye is strongly dependent on its proximity to another light absorbing moiety or quencher. These dyes and quenchers are typically attached to a DNA sequence-specific probe or primer. Among the FRET-based detection chemistries are hydrolysis probes and conformation probes. Hydrolysis probes (such as the Taq-Man® probe) use the polymerase enzyme to cleave a reporter dye molecule from a quencher dye molecule attached to an oligonucleotide probe. Conformation probes (such as molecular beacons) utilize a dye attached to an oligonucleotide, whose fluorescence emission changes upon the conformational change of the oligonucleotide hybridizing to the target DNA.

A number of commercial instruments exist that perform real-time PCR. Examples of available instruments include the Applied Biosystems PRISM 7500, the Bio-Rad iCylcer, and the Roche Diagnostics LightCycler 2.0. The sample containers for these instruments are closed tubes which typically require at least a 10 µl volume of sample solution. If the lowest concentrations of template DNA detectable by a particular assay were on the order of one molecule per microliter, the detection limit for available instruments would be on the order of tens of targets per sample tube. Therefore, in order to achieve single molecule sensitivity, it is desirable to test smaller sample volumes, in the range of 1-1000 nl.

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones.

For example, Lagally et al. (*Anal Chem* 73:565-570 (2001)) demonstrated amplification and detection of single template DNA in a 280 nl PCR chamber. Detection of products was made post-PCR using capillary electrophoresis. On the other hand, Kopp et al. (*Science* 280:1046-1048 (1998)) demonstrated continuous-flow PCR using a glass substrate with a serpentine channel passing over three constant temperature zones at 95° C. (denature), 72° C. (extension), and 60° C. (annealing). The 72° C. zone was located in the central region and had to be passed through briefly in going from 95° C. to 60° C. Detection was made post-PCR using gel electrophoresis. Since this PCR technique is not based on heating the entire surfaces of the reaction vessel, the reaction rate is determined by a flow rate, not a heating/cooling rate. Neither of these references described real-time monitoring of the PCR reaction.

Park et al. (*Anal Chem* 75:6029-6033 (2003)) describe a continuous-flow PCR device that uses a polyimide coated fused silica capillary wrapped into a helix around three temperature-controlled blocks. Sample volumes were 2 µl. Detection was made post PCR using gel electrophoresis. Reference was made to the possibility of adapting their instrument for real-time PCR by using a capillary coated with PTFE instead of non-transparent polyimide. See also, Hahn et al. (WO 2005/075683).

Enzelberger et al. (U.S. Pat. No. 6,960,437) describe a microfluidic device that includes a rotary channel having three temperature zones. A number of integrated valves and pumps are used to introduce the sample and to pump it through the zones in a rotary fashion.

Knapp et al. (U.S. Patent Application Publication No. 2005/0042639) describe a microfluidic device capable of single molecule amplification. A planar glass chip with several straight parallel channels is disclosed. A mixture of target DNA and PCR reagents is injected into these channels. In a first embodiment, the channels are filled with this mixture and flow is stopped. Then the entire length of the channels is thermally cycled. After thermal cycling is completed, the channels are imaged in order to detect regions of fluorescence where DNA has been amplified. In a second embodiment, the PCR mixture flows continuously through the amplification zone as the temperature is cycled, and fluorescence is detected downstream of the amplification zone. Different degrees of amplification are achieved by altering the time spent in cycling, through changing distance traveled under cycling, and the like. It is worth noting that this method varies conditions (such as cycles experienced) for separate consecutive sample elements, rather than monitoring the progress of individual sample elements over time.

None of this art has combined single target molecule sensitivity with real-time reaction monitoring capability in a continuous flow device. Thus, a need exists for robust high throughput methods of real-time PCR that can be performed efficiently and accurately with small sample volumes. It would be desirable that the methods have single target molecule sensitivity, use lower quantities of PCR reagents and use less energy for temperature cycling. The present invention provides these and other features that will be apparent upon review of the description of the invention.

SUMMARY OF THE INVENTION

The present invention relates to methods for amplifying nucleic acids in micro-channels. More specifically, the present invention relates to methods for performing a real-time polymerase chain reaction (PCR) in a continuous-flow microfluidic system and to methods for monitoring real-time PCR in such systems.

Thus, in a first aspect, the present invention provides a method of performing real-time PCR comprising the steps of: a) continuously moving a bolus of test solution containing real-time PCR reagents in a channel; b) moving a carrier-fluid in the channel, sequentially alternating with a test bolus; c) cycling the temperature in a defined section of the channel in order to achieve PCR; and d) measuring the intensity of the fluorescent signal at a plurality of locations along the defined section of the channel. In one embodiment, the channel is a micro-channel or a microfluidic channel, such that the dimensions of the channel are small enough to allow for the amplification and detection of a single DNA molecule originally present in the test solution. In another embodiment, the test solution is substantially the same as the carrier fluid, except that it comprises all the necessary real-time PCR reagents. The real-time PCR reagent mixture may include PCR primers, dNTPs, polymerase enzymes, salts, buffers, surface-passivating agents, and the like. In addition, the real-time PCR mixture may include a non-specific fluorescent DNA detecting molecule, a sequence-specific fluorescent DNA probe or a marker. In an additional embodiment, the carrier fluid is an immiscible fluid. The purpose of the carrier fluid is to deter transfer of material from one test bolus to another. Another purpose of the carrier fluid is to provide a distinguishable transition between boluses that may be used to track the fluid flow in the channel. The carrier fluid may include a marker.

In one embodiment, the temperature is cycled using a thermal transfer element along the defined section of the channel. In another embodiment, the thermal transfer element cycles the temperature in the entire defined section of the channel. That is, a constant temperature zone is used to provide the thermal cycling. In a further embodiment, an appropriately programmed computer controls the temperature cycling of the thermal transfer element. In one embodiment, the temperature of the thermal transfer element is detected and fed back to the computer. In accordance with these embodiments, heating and cooling are applied to a length of the channel (the reaction zone) such that its temperature follows a PCR profile in time. The test boluses are pumped through this reaction zone at a flow rate (speed) such that the number of PCR cycles required is achieved during the time the bolus flows from the upstream end to the downstream end of the reaction zone.

In another embodiment, the intensity of the fluorescent signal is measured at a specific time and/or temperature during the PCR temperature cycle. In an additional embodiment, the intensity of the fluorescent signal is measured once during each PCR cycle. In a further embodiment, the plurality of locations at which the intensity of the fluorescent signal is measured is the entire defined section of the channel. In another embodiment, the data concerning the intensity of the fluorescent signal is processed by an appropriately programmed computer. In another embodiment, an image of at least one fluorescent signal along the length of the channel is made. In a further embodiment, the image capture is performed repeatedly on consecutive temperature cycling periods. The image may be created or the intensity of the fluorescent signal measured using a multiple-pixel array detector. A stationary mechanism or a scanning mechanism or both may be used to capture the image.

In a second aspect, the present invention provides a method for performing real-time PCR that includes monitoring the average flow speed of the liquid in a channel. In accordance with this aspect, the method comprises the steps as set forth in the first aspect and further comprises the step of: e) measuring the average flow speed of the fluid in the channel. By monitoring the flow speed in the channel, the location of a test bolus as a function of time can be determined, thus identifying the number of PCR cycles that has been experienced by the test bolus.

In one embodiment, average flow speed of the fluid is measured by comparing sequential images of the reaction-dependent fluorescent signal from the channel. In a second embodiment, the average flow speed of the fluid is measured by comparing sequential images of a marker (i.e., a reaction independent marker) in the channel. The use of the marker has the advantage that if the real-time PCR signal is not detectable, the fluid flow would still be detectable. Examples of potential markers are dyes, semiconductor quantum dots, polymer microbeads, scattering metal particles, microbubbles, and the like known to skilled artisans. In one embodiment, the marker is present in the test solution. If the marker is present in the test solution, it should not adversely affect any PCR chemical reactions. In another embodiment, the marker is present in the carrier fluid. In a further embodiment, the marker is a separate bolus in series with test boluses. In an additional embodiment, the marker is resolvable from the fluorescent signal, such as by excitation wavelength, emission spectrum, lifetime, and the like well known in the art. In a further embodiment, the data concerning the sequential images of the intensity of the fluorescent signal or of the marker is processed by an appropriately programmed computer. In accordance with these embodiments, the average flow speed is determined by comparing images taken from consecutive PCR cycles. In a still further embodiment, the flow speed can be measured using a reaction zone entrance detector and a volume flow rate meter. Flow speed could be estimated, for example, by knowing the dimensions of the channel and measuring the volume flow rate.

In a third aspect, the present invention provides a method for performing real-time PCR that includes monitoring the flow speed of the liquid in a channel and adjusting the flow speed as necessary to control the duration of the PCR cycling experienced by a test solution or test sample. In accordance with this aspect, the method comprises the steps as set forth in the second aspect and further comprises the step of: f) adjusting the flow speed of the fluid to control the duration of the PCR cycling. In one embodiment, the flow speed is monitored and adjusted such that the desired number of PCR cycles is completed while the test solution is moving through the defined section of the channel. That is, the flow speed is adjusted to determine the duration of the PCR cycling. In another embodiment, this monitoring and adjustment is performed by an appropriately programmed computer. In a further embodiment, the flow rate is adjusted by regulating the pressure at the input end of the channel. In an additional embodiment, the flow rate is adjusted by regulating the pressure regulated vacuum at the output end of the channel. In another embodiment, the flow rate is adjusted by regulating a pump, such as a syringe pump.

In a fourth aspect, the present invention provides method for monitoring the progress of a polymerase chain reaction in a channel comprising the steps of: a) moving a bolus of test solution containing real-time PCR reagents in a channel; b) moving a carrier fluid in said channel, sequentially alternating with a test bolus; c) cycling the temperature in a defined section of the channel in order to achieve PCR; d) capturing an image of a reaction-dependent fluorescence signal along a section of the channel; e) measuring the average flow speed in the channel; and f) relating position of the test bolus to the number of temperature cycles experienced by a test bolus from the average flow rate. In one embodiment, the average flow speed is measured by comparing sequential images of the reaction-dependent fluorescent signal from the channel. In a second embodiment, the average flow speed is measured by comparing sequential images of a reaction-independent flow marker from the channel. The reaction-independent flow marker may be (i) pre-mixed in the test bolus, (ii) introduced to the channel as a bolus alternating with the test bolus or (iii) pre-mixed in the carrier fluid. In another embodiment, scattered light from the reaction-independent flow marker is resolvable from the reaction-dependent fluorescence by wavelength spectrum. In an alternative embodiment, scattered light from the reaction-independent flow marker is resolvable from the reaction-dependent fluorescence on the basis of fluorescence lifetime. In another embodiment, the reaction-independent flow marker is further used to determine the flow dispersion of the test bolus. In a further embodiment, the image of reaction-dependent fluorescence is captured at least once per PCR cycle. In one embodiment, the image of reaction-dependent fluorescence is captured sequentially by scanning a length of the channel on a time scale shorter than the duration of one PCR cycle. In an alternative embodiment, the image of reaction-dependent fluorescence is captured by acquiring signal from multiple points along the channel simultaneously. In another embodiment, the flow speed measurements are part of a feedback loop for regulating the flow speed. In a further embodiment, the flow speed is measured through detecting a sample bolus entrance into and exit from a defined section of the channel.

In a fifth aspect, the present invention provides a method for monitoring the progress of a polymerase chain reaction in a channel, comprising the steps of: a) moving a bolus of test solution containing real-time PCR reagents in a channel; b) moving a carrier fluid in the same channel, sequentially alternating with a test bolus; c) applying spatial temperature zones along the channel to achieve PCR; d) monitoring the fluorescence signal at fixed spatial locations along the channel corresponding to fixed points in the PCR cycle; e) measuring the average flow speed of the fluid in the channel; and f) adjusting the flow rate in order to control the timing of the PCR cycle. In one embodiment, the temperature is cycled using a thermal transfer element along portions of the channel. In another embodiment, the thermal transfer element cycles the temperature in the portions of the channel. In a further embodiment, an appropriately programmed computer controls the temperature cycling of the thermal transfer element. In one embodiment, the temperature of the thermal transfer element is detected and fed back to the computer. In accordance with these embodiments, heating and cooling are applied to portions of the channel such that a PCR temperature profile is followed. The test boluses are pumped through this reaction zone at a flow rate (speed) such that the number of PCR cycles required is achieved during the time the bolus flows from the upstream end to the downstream end of the reaction zone. By monitoring the flow speed in the channel in this aspect of the invention, the duration of the PCR cycle period can be determined.

In a sixth aspect, the present invention provides systems and/or kits adapted for practicing the methods described herein. The systems and/or kits can include system instructions (e.g., embodied in a computer or in a computer readable medium, e.g., as system software) for practicing any of the method steps herein. Fluid handling elements for storing, transferring, aliquotting, or diluting samples, e.g., microfluidic handling elements, and detector elements can also be components of the systems and kits herein. In addition, packaging materials, integration elements (e.g., instrument cases, power supplies, etc.), instructions for using the systems and kits and the like can be features of the invention.

In one embodiment, the invention provides a system that includes a microfluidic device comprising one or more amplification channels each configured to thermocycle one or more test solutions. A thermal transfer element for cycling the temperature along a defined section of the channel(s) is also included. The thermal transfer element is integral with or proximal to the microfluidic device. A source of illumination integral with or proximal to the microfluidic device is also included, where the source of illumination is configured to illuminate the channel(s). A detector integral with or proximal to the microfluidic device is also included, where the detector is configured to detect the amplification products and/or marker in the channel(s). In one embodiment, the detector can independently detect signals from two or more detectable markers with different signals; e.g., a detector that can simultaneously detect fluorescent or other emissions at two or more wavelength ranges. The system includes one or more elements for controlling the flow rate of the continuously moving test solution and carrier fluid in the channel(s), as well as system instruction or software for monitoring and controlling the flow rate in order to control the timing of each PCR cycle. Typically, the system includes a sensor to detect the temperature of the thermal transfer element and to provide feedback information for controlling the temperature cycles. Typically, the system also includes system software for generating and processing data, such as timing the detection of the amplified products and/or marker, monitoring location of test solutions in the channel(s) and the like.

In a second embodiment, the system may also include a dilution module that dilutes the sample into multiple test solutions, as well as system instructions that direct the dilution module to aliquot the sample into a plurality of test solutions. The dilution module may be integral with or proximal to the microfluidic device.

The system optionally comprises software with instructions for performing any of the method steps described herein. For example, the system can include statistical or probabilistic system software that performs one or more statistical or probabilistic analysis of signals received from one or more of the test solutions subjected to thermocycling. For example, the statistical or probabilistic analysis can include Poisson analysis, Monte Carlo analysis, application of a genetic algorithm, neural network training, Markov modeling, hidden Markov modeling, multidimensional scaling, PLS analysis, and/or PCA analysis. The statistical or probabilistic analysis optionally comprises quantitatively determining a concentration, proportion, or number of the nucleic acids of interest in the sample.

The system also optionally includes fluid handling or storage features such as sample storage modules that store the samples until they are to be diluted by the dilution module, a sample retrieval module that retrieves the sample from the sample storage module and delivers it to the dilution module, or the like. These features are optionally designed to provide for continuous flow of fluid (e.g., comprising the sample) through the system (thereby providing for higher sample throughput). The system may also include means and system software for analyzing the amplified product. In one embodiment, the system may include system software that correlates a reproducible signal shape, length, width, volume or area occupied by the amplification products, as detected by the detector, to (a) the number of copies of the nucleic acid of interest present in one of the test solutions, or to the number of copies of the nucleic acid of interest present in the sample, or both or (b) an identification of the amplification product(s) present in the sample or (c) any other analytical parameters known and used in the art.

Many of the above methods or systems can be used in combination. Additional features of the invention will become apparent upon review of the following description.

BRIEF DESCRIPTION OF THE FIGURES

The file of this patent contains at least one drawing executed in color photograph. Copies of this patent with color photograph(s) will be provided by the Patent and Trademark Office upon request and payment of the necessary fee.

FIG. 2 shows a schematic illustration of a real-time PCR microfluidic system in accordance with one embodiment of the present invention.

FIG. 4 shows a schematic illustration of a real-time PCR microfluidic system in accordance with another embodiment of the present invention.

DETAILED DESCRIPTION OF THE INVENTION

The present invention relates to methods for amplifying nucleic acids in micro-channels. More specifically, the present invention relates to methods for performing a real-time polymerase chain reaction (PCR) in a continuous-flow microfluidic system and to methods for monitoring real-time PCR in such systems.

Unless defined otherwise, all technical and scientific terms used herein have the same meaning as commonly understood by one of ordinary skill in the art to which the invention pertains. Although any methods and materials similar or equivalent to those described herein can be used in the practice of the present invention, the preferred materials and methods are described herein.

Figure 1:
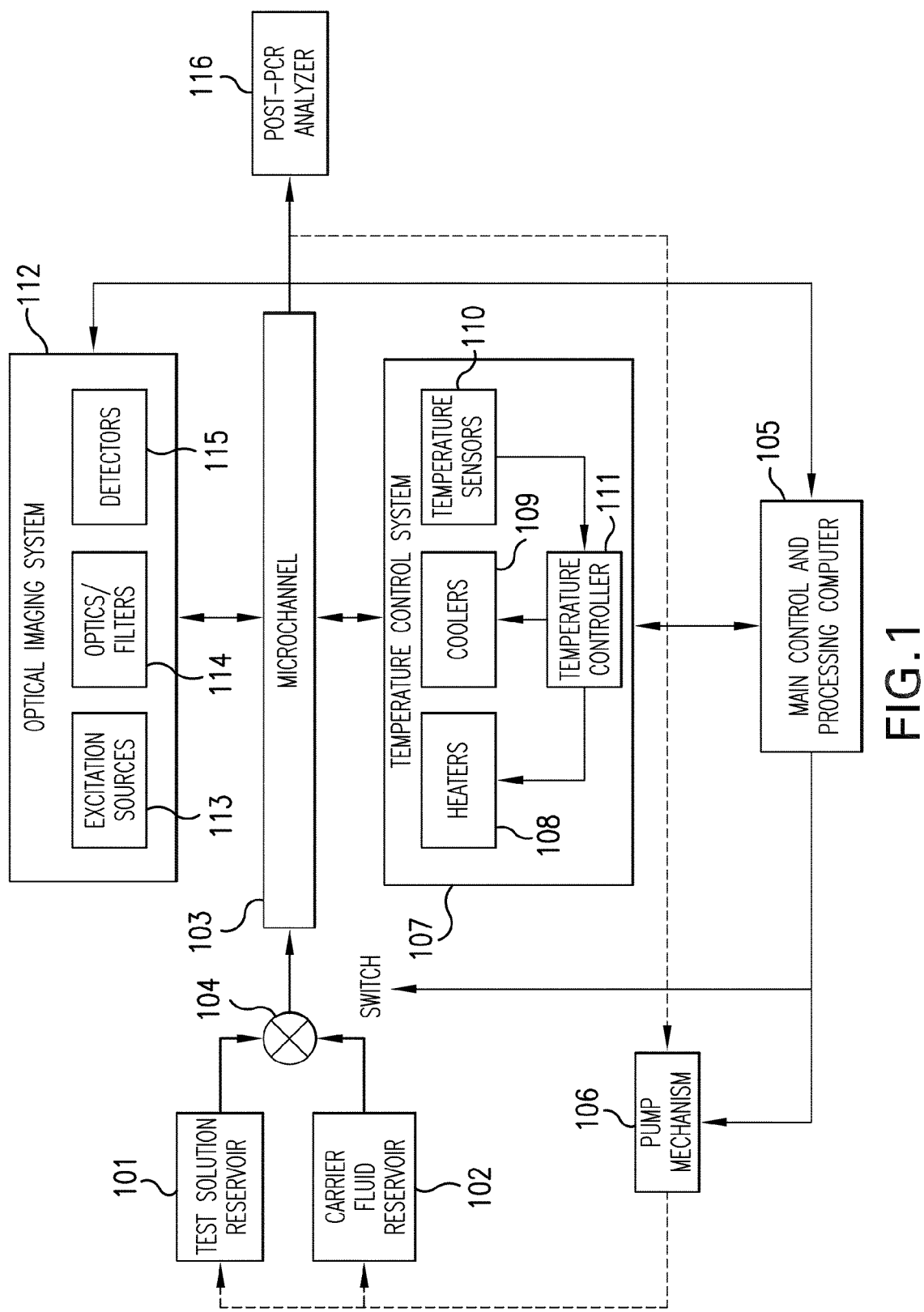
FIG. 1 shows a block diagram of a real-time PCR architecture in accordance with one embodiment of the present invention.

FIG. 1 illustrates a block diagram of a real-time PCR architecture in accordance with one embodiment of the present invention. The system includes a test solution reservoir 101, which as described above, may be a reservoir containing multiple test solutions, such as a microtiter plate in which each well contains different test solutions, e.g., test samples. The system further includes a carrier fluid reservoir 102. In one embodiment, the test solution is substantially the same as the carrier fluid, except that the test solution comprises all the necessary real-time PCR reagents. The real-time PCR reagent mixture may include PCR primers, dNTPs, polymerase enzymes, salts, buffers, surface-passivating agents, and the like. In addition, the real-time PCR mixture may include a non-specific fluorescent DNA detecting molecule, a sequence-specific fluorescent DNA probe or a marker. In an additional embodiment, the carrier fluid is an immiscible fluid (such as an oil, a fluorinated liquid, or any other nonaqueous or hydrophobic solvent). The purpose of the carrier fluid is to deter transfer of material from one test bolus to another. Another purpose of the carrier fluid is to provide a distinguishable transition between boluses that may be used to track the fluid flow in the channel. In one embodiment, the carrier fluid may include a marker.

Figure 6:
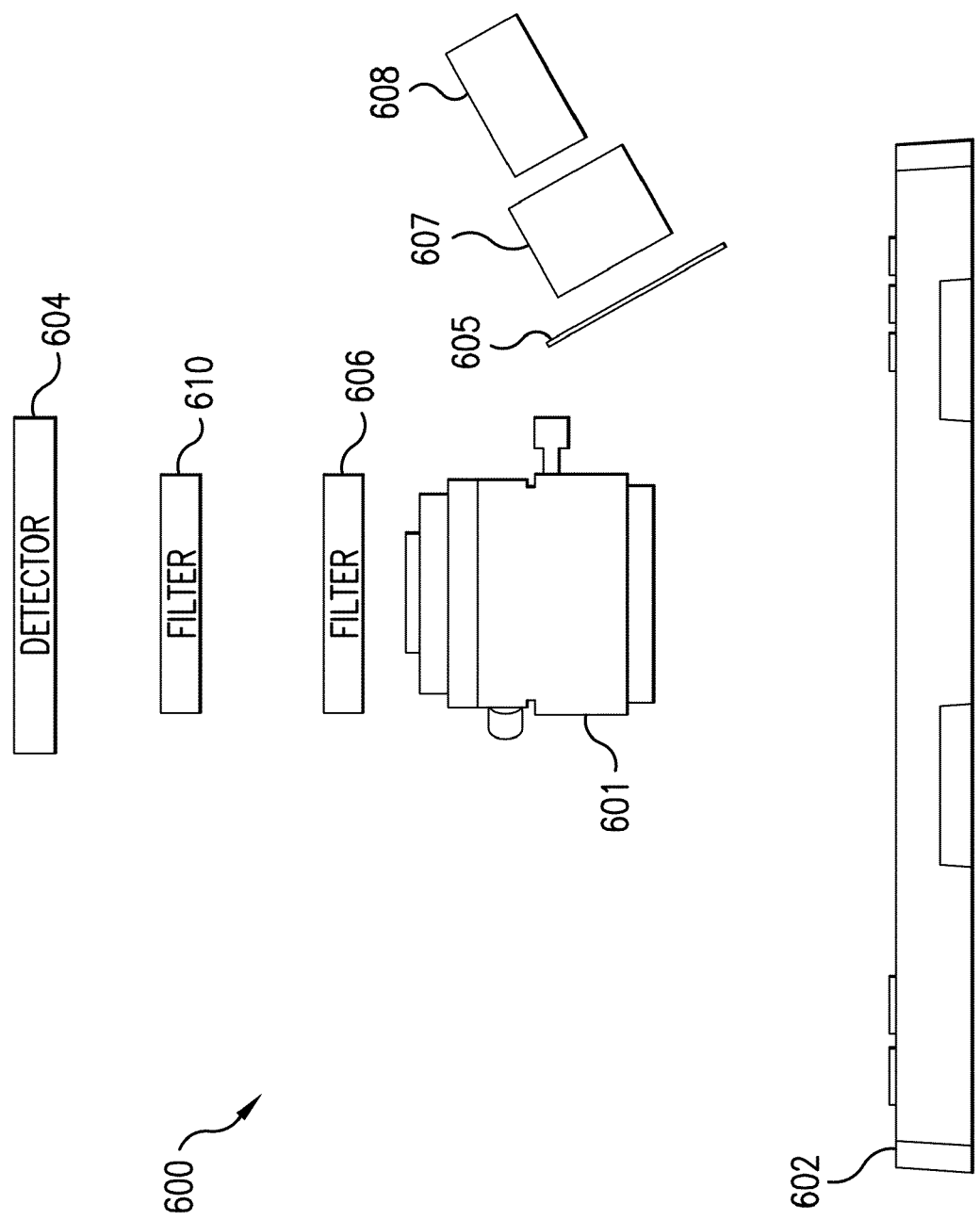
FIG. 6 shows a system that is useful for quantitative PCR in real-time in a microfluidic device in accordance with yet another embodiment of the present invention.

In one embodiment, the test solution and carrier fluid are introduced into a microchannel 103 through a switch 104. The dimensions of the microchannel are small enough to allow for the amplification and detection of a single DNA molecule originally present in the test solution. Microchannel 103 may be a single microchannel or it may be one of several microchannels that are part of a microfluidic device (such as shown in FIGS. 2, 4 and 6). Switch 104 is under control of a main control and processing computer 105 such that the carrier fluid and the test solution are sequentially alternately introduced into microchannel 103. The volume of the test solution and carrier fluid that is introduced into microchannel 103 is selected such that there is minimal blending between them during movement through microchannel 103.

A multitude of reactions in series (or sequential reactions) can thus be carried out in the same microchannel 103 as a result of the continuous movement of different test solutions through microchannel 103 each separated by the carrier fluid. If microchannel 103 is one of several microchannels in a microfluidic device, then a multitude of reactions can also be carried out in parallel in the microchannels of the microfluidic device. The flow rate of the carrier fluid and test solution through microchannel 103 is controlled by pump mechanism 106. Pump mechanism 106 is under control of main control and processing computer 105 in order to regulate the flow rate of the test solution and the carrier fluid in microchannel 103. The flow rate is regulated such that a desired number of PCR cycles are performed as the test solution passes through microchannel 103.

Pump mechanism 106 can regulate the flow rate of the test solution and carrier fluid by positive pressure at the upstream side or inlet of microchannel 103 or by negative pressure at the downstream side or outlet of microchannel 103. In one embodiment, the pressure difference is approximately 1 psi, although other pressure differences may be utilized. The length of microchannel 103 is suitable for the completion of the desired number of PCR cycles such as, for example, 10 to 50 cycles of PCR, or any number in between, as the test solution moves through the reaction zone of microchannel 103. The reaction zone of microchannel 103 is the region of the microchannel in which the temperature is cycled for conducting the PCR cycles. Typically, 25-30, 25-35, 25-40, 30-35, 30-40 or 35-40 PCR cycles are performed for standard amplification reactions. The length of microchannel 103 to accomplish the desired number of PCR cycles is also dependent on the volume of test solution and carrier fluid that are sequentially alternately moved through microchannel 103. For example, if the reaction zone is 40 mm, then the minimum volume of test solution would occupy 1 mm in the reaction zone of microchannel 103, and the maximum volume of test solution would occupy 20 mm in the reaction zone of microchannel 103. Thus, in this non-limiting example, a minimum of 1 sample and a maximum of 20 samples could be amplified as the test solution moves through the reaction zone of microchannel 103. Of course, the microchannel length and sample volumes can be selected to amplify any number of samples.

A temperature control system 107 is included in the system to control and cycle the temperature to produce suitable temperatures for the PCR cycles as the test solution moves through microchannel 103. Suitable temperatures for the PCR cycles are well known to skilled artisan and may include a first temperature in the range of about 85° C. to about 100° C., a second temperature in the range of about 20° C. to about 70° C. and a third temperature in the range of about 55° C. to about 80° C. Temperature control system 107 is integral with or proximal to microchannel 103 or to the microchannels of a microfluidic device. Temperature control system 107 includes heaters 108, coolers 109, temperature sensors 110 and a temperature controller 111. Temperature controller 111 collects temperature information from the temperature sensors 110 and generates control signals based on the temperature information. The control signals are sent to the heaters 108 or coolers 109 to cycle the temperature in microchannel 103 for the desired PCR cycles. Temperature controller 111 is under control of main control and processing computer 105 so that the temperature is cycled such that the desired number of PCR cycles is performed as the test solution moves through microchannel 103. The different PCR reactions in the different test solutions follow one after another in microchannel 103 in a serial manner due to the continuous flow in microchannel 103.

In one embodiment, the heating and cooling may be accomplished by blowing air of the appropriate temperatures. In another embodiment, the heating and cooling may be accomplished by circulating water or fluid baths. In an additional embodiment, the heating and cooling may be accomplished by Peltier-effect elements which are well known to the skilled artisan. Junctions of different metals, which are crossed by an electric current, make it possible to cool or heat a small surface. A temperature probe on the Peltier element makes it possible to regulate the power, which is proportional to the electrical intensity, and thus makes it possible to regulate the temperature. In a further embodiment, a metal block is used as a thermal transfer element and includes a thermoelectric cooler in contact with the metal block. This metal block can be made of any metal (or metal alloy) having suitable thermal transfer properties such as, for example, aluminum. In order to reduce backscatter of light from the metal block it is preferably painted black or anodized. The temperatures for the PCR cycles can equilibrate at suitable time intervals for this thermal transfer unit. For example, the temperatures for the PCR cycles can equilibrate within approximately 1-2 seconds or even faster.

In one embodiment, temperature control system 107 cycles the temperature in an entire defined section of microchannel 103, i.e., that section of microchannel 103 in which the PCR cycles are performed. This defined section of microchannel 103 is also known as the reaction zone. Thus, in this embodiment a constant temperature zone is used to provide the thermal cycling. An appropriately programmed computer controls the temperature cycling of the thermal transfer element. In accordance with this embodiment, heating and cooling are applied to a length of the channel (the reaction zone) such that its temperature follows a PCR profile in time. The test boluses are pumped through this reaction zone at a flow rate (speed) such that the number of PCR cycles required is achieved during the time the bolus flows from the upstream end to the downstream end of the reaction zone.

In a second embodiment, temperature control system 107 applies spatial temperature zones along microchannel 103 to achieve a polymerase chain reaction. In one aspect, the temperature is cycled using a thermal transfer element along portions of the microchannel 103 or the microchannels of a microfluidic device. In another aspect, the thermal transfer element cycles the temperature in portions of microchannel 103. An appropriately programmed computer controls the temperature cycling of the thermal transfer element. In accordance with this embodiment, heating and cooling are applied to portions of the channel such that a PCR temperature profile is followed. The test boluses are pumped through this reaction zone at a flow rate (speed) such that the number of PCR cycles required is achieved during the time the bolus flows from the upstream end to the downstream end of the reaction zone.

An optical imaging system 112 is included in one embodiment of the present invention to detect the amplification product and to monitor the flow rate of the test solution in microchannel 103. In one embodiment, the optical imaging system 112 is a fluorescent imaging system that preferably includes one or more excitation sources 113, one or more optics/filters 114 and one or more detectors 115. In one embodiment, excitation sources 113 generate light at desired wavelengths to excite the labels used for detecting the amplification products during real-time PCR and/or to detect markers that may be present to monitor the flow rate of the test solution in microchannel 103. Optics/filters 114 are used to form a beam of light and/or to direct the light from excitation sources 113 to the appropriate positions on the microchannel 103. Optics/filters 114 are also used to filter the light to exclude light of undesired wavelengths or to reduce backscatter from reaching detectors 115. The desired wavelengths to excite the labels used in real-time PCR will depend on the precise labels and/or markers used, e.g., intercalating dyes, molecular beacons, quantum dots or TaqMan® probes, which wavelengths are well known to skilled artisans. Similarly, the emission wavelengths of the precise labels and/or markers are well known to skilled artisans. Detectors 115 detect the emission wavelengths of the excited labels and/or markers and measure the intensity of the emitted light. Optical imaging system 112 preferably is able to distinguish between multiple microchannels in a microfluidic device.

Optical imaging system 112 is under control of main control and processing computer 105 which directs the optical/fluorescence imaging system 112 to measure the intensity of the emitted light at desired time intervals, such as, for example, at least once during each PCR cycle at a plurality of locations in microchannel 103 or in the microchannels of a microfluidic device. Detectors 115 generate a signal or an image of the intensity of the emitted light and direct it to main control and processing computer 105 for analysis of the amplification product and for monitoring the flow rate of the test solution. Detectors 115 may include multiple-pixel array detectors (such as a CCD detector) and/or discrete single-pixel or non-imaging detectors. Detectors 115 may be integral with or proximal to microchannel 103 or to the microchannels of a microfluidic device. Detectors 115 may be stationary or may be scanning. The detectors 115 should have appropriate resolution for obtaining meaningful results and for monitoring of fluid flow in microchannel 103, particularly because the fluid is continuously moving in microchannel 103.

As described above, the real-time PCR mixture may include a non-specific fluorescent DNA detecting molecule (such as an intercalating dye), a sequence-specific fluorescent DNA probe (such as a molecular beacon, a TaqMan® probe or a quantum dot probe), or a flow marker (such as a quantum dot), and the carrier fluid may include a flow marker. In one embodiment, the optical imaging system 112 is utilized to detect the intensity of the fluorescence from the DNA detecting molecule or the probe (i.e., the intensity of the fluorescent signal) and/or to detect the fluorescence of the marker. The fluorescence of the marker can be used to delineate the test solution from the carrier fluid and can also be used to determine and monitor the flow speed of the test solution or carrier fluid. The intensity of the fluorescent signal can be used to detect amplified product, to determine the quantity of amplified product, to determine the number of original molecules present in the test solution, and the like as well known to a skilled artisan for real-time PCR. The intensity of the fluorescent signal can also be used to determine and monitor the flow speed of the test solution.

In one embodiment, the intensity of the fluorescent signal is measured (e.g., an image of the fluorescent signal is taken) at a specific time and/or temperature during the PCR temperature cycle. In another embodiment, the intensity of the fluorescent signal is measured once during each PCR cycle. The optimal time to capture the image depends on the chemistry utilized. For example, if an intercalating dye is used to detect amplified product, the image should be captured at the end of the extension phase of the PCR cycle. If a TaqMan® probe is used to detect the amplified product, the image could be captured at any time during the PCR cycle. Main control and processing computer 105 can be programmed to take the image at the time and temperature desired. In a further embodiment, the intensity of the fluorescent signal is measured at a plurality of locations. The plurality of locations at which the intensity of the fluorescent signal is measured may be different sections of the microchannel. The plurality of locations at which the intensity of the fluorescent signal is measure may be the entire defined section (i.e., reaction zone) of the microchannel. In another embodiment, an image of at least one fluorescent signal along the length of the channel is made. In a further embodiment, the image capture is performed repeatedly on consecutive temperature cycling periods. The image may be created or the intensity of the fluorescent signal measured using a multiple-pixel array detector (such as a CCD or CMOS image sensor) or a single pixel detector. Fluorescent light may be collected using large field-of-view imaging optics and/or small field-of-view optics such as a fiber-optic/lens combination. A stationary mechanism or a scanning mechanism or both may be used to capture the image. The data concerning the intensity of the fluorescent signal is processed by an appropriately programmed computer.

After test solution has moved through microchannel 103 and completed the desired number of PCR cycles, it may optionally be sent to a post-PCR analyzer 116. Post-PCR analyzer 116 may include any analytical technique that can be used on PCR amplification products. Such techniques include, but are not limited to, sequencing, electrophoresis, probing, melt curve analysis, and the like.

Figure 3A:
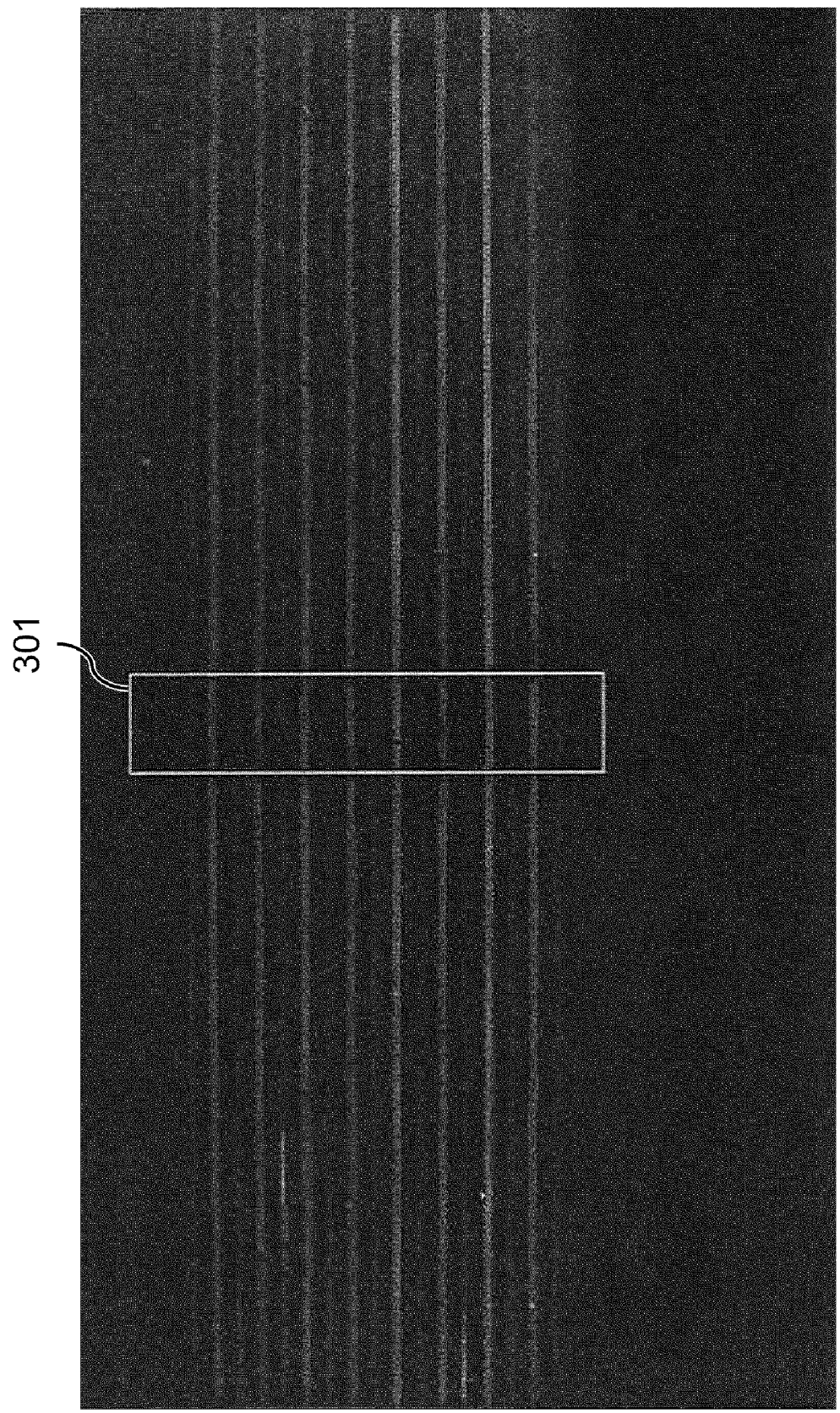
FIGS. 3A and 3B shows a sensor output image with data processing from the system of FIG. 2.
Figure 3B:
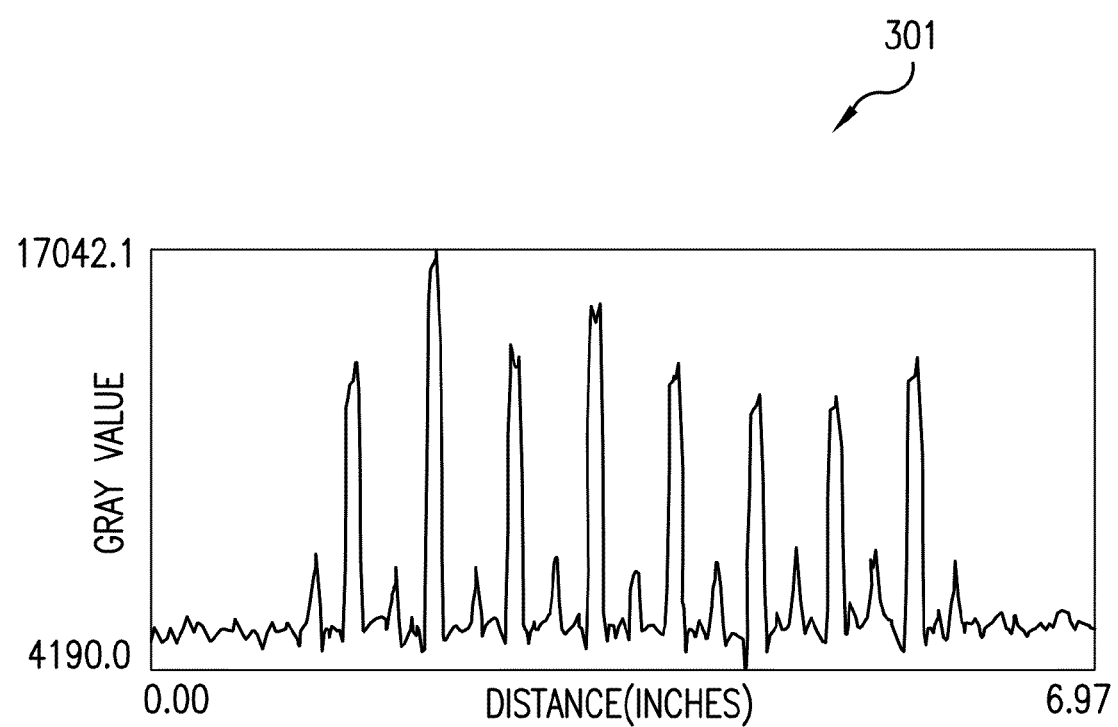

Examples of systems useful for real-time PCR in microchannels in accordance with the present invention are shown schematically in FIGS. 2, 4 and 6. In FIG. 2, a real-time PCR system 200 is illustrated with a microfluidic device 201 that contains multiple microchannels. Because there is an effect of gravity on the fluid in the microchannels, microfluidic device 201 is preferably oriented such that the test and carrier fluids flow in a generally horizontal direction. However, microfluidic device 201 may be oriented in such that the carrier and test fluids flow in other directions including the vertical direction. A thermal transfer element is located proximal to microfluidic device 201. The optical imaging system includes an illumination laser 202 and a beam forming lens 203 for illuminating the microchannels in microfluidic device 201 with the appropriate excitation wavelength(s). The optical imaging system further includes a filter 204 for filtering the emission wavelength(s) and reducing backscatter and a multiple-pixel array detector 205. The real-time PCR system 200 may also optionally include a lens 207. A sensor output image with data processing using this system is shown in FIGS. 3A and 3B. FIG. 3A shows a two dimensional image of 8 parallel microfluidic channels filled with 100 nM FAM fluorescent dye. FIG. 3B shows a profile plot of the region of interest box 301 of FIG. 3A.

Figure 5:
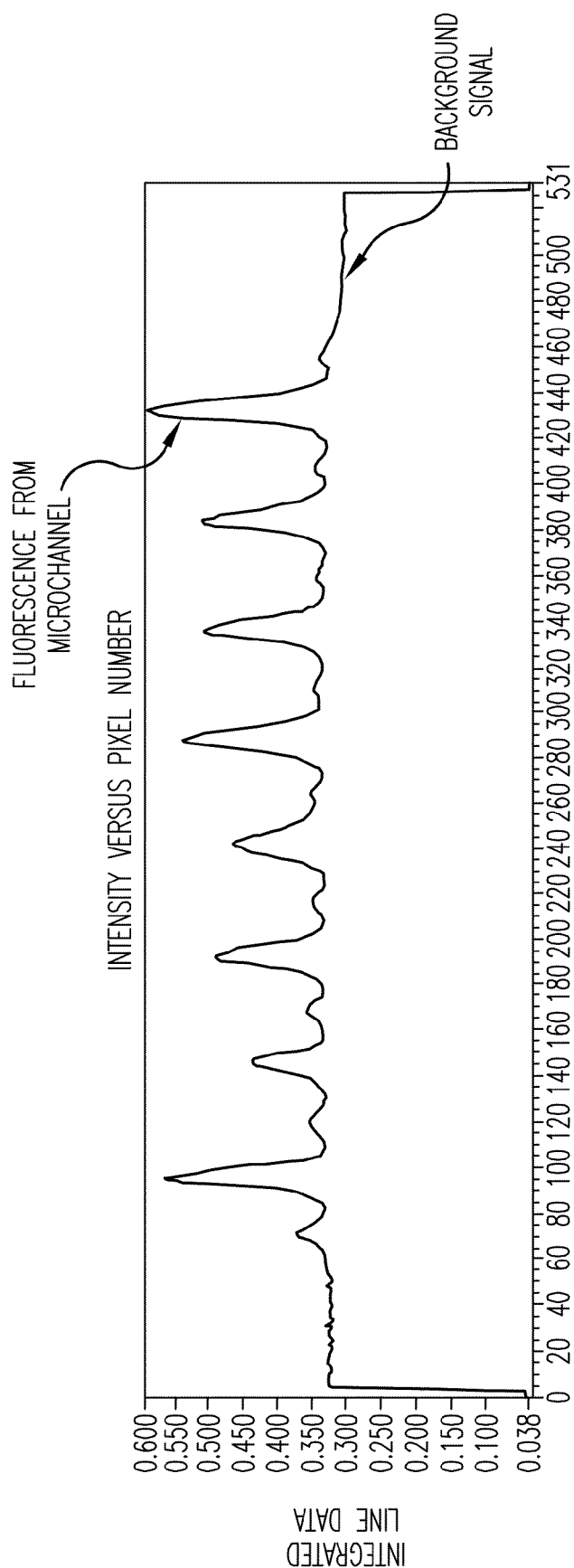
FIG. 5 shows sensor output data from the system of FIG. 4 in accordance with the present invention.

In FIG. 4, a system 400 for real-time PCR is illustrated with a microfluidic device 401 that contains multiple microchannels. A thermal transfer element (not shown) is proximal to microfluidic device 401. The optical imaging system includes an illumination laser 402 and a beam forming lens 404 for illuminating the microchannels in microfluidic device 401 with the appropriate excitation wavelength(s). The optical imaging system further includes a filter 405 for filtering the emission wavelength(s) and reducing backscatter and a CCD detector 406. The real-time PCR system 400 may also optionally include a lens 403. Sensor output data from a 512 pixel linear CCD array sensor using this system is shown in FIG. 5. The microchannels were filled with 100 nM FAM fluorescent dye to demonstrate this sensor output data. The peaks show the fluorescence from the microchannel. In this embodiment, the laser beam and detector field of view are scanned with respect to the length of the microchannel, in order to measure fluorescence as a function of position along the channel.

A system useful for real-time PCR in a microfluidic device is illustrated in FIG. 6 which is capable of multi-color sensing from multiple fluorophores. In this embodiment, real-time PCR system 600 includes a microfluidic device 602 which preferably includes multiple microchannels and a thermal element (not shown) located proximal to microfluidic device 602. This embodiment further includes a light source 608 that is capable of emitting light at multiple wavelengths such as, for example, red and blue light, for providing multi-color excitation light to the channels in microfluidic device 602. In one aspect of this embodiment, the light source 608 includes multiple LEDs which emit light at different wavelengths. The real-time PCR system 600 further includes an excitation filter 607 and a dual bandpass interference filter 605 that passes light at the multiple excitation wavelengths (such as red light and blue light). The system 600 also includes a lens 601 for collecting the emitted light, for example, from a fluorophore in the amplification product and a different fluorophore in a flow marker, and directing it to detector 604. In one embodiment, an emission filter 606 is also provided for blocking excitation light and passing the fluorescent light from the fluorophores. Detector 604 can be a multiple pixel array which is capable of multicolor sensing such as, for example, CMOS image sensor.

In a preferred embodiment, the system 600 further includes a color filter array 610 for arranging RGB colors on the detector 604 which enables simultaneous imaging of multiple colors. The color filter array 610 could be, for example, a Bayer filter. The multi-color system of the present invention enables simultaneous imaging of multiple colors which provides, for example, DNA and flow marker detection utilizing different fluorophores.

The systems described herein are specifically adapted for methods of performing real-time PCR in a microchannel and methods for monitoring the progress of a polymerase chain reaction in a microchannel. In one embodiment of the methods in accordance with the present invention, a bolus of test solution is continuously moved in the microchannel. The test solution contains real-time PCR reagents as described above. A carrier fluid is continuously moved in the microchannel. The carrier fluid sequentially alternates with a test bolus. The temperature is cycled in a defined section of the microchannel in order to achieve PCR. The intensity of the fluorescent signal is measured at a plurality of locations along the defined section of the microchannel. Thus, in accordance with this embodiment, a method for performing real-time PCR comprises the steps of: a) continuously moving a bolus of test solution containing real-time PCR reagents in a channel; b) moving a carrier-fluid in the channel, sequentially alternating with a test bolus; c) cycling the temperature in a defined section of the channel in order to achieve PCR; and d) measuring the intensity of the fluorescent signal at a plurality of locations along the defined section of the channel.

In one embodiment, the temperature is cycled using a thermal transfer element along the defined section of the channel. In another embodiment, the thermal transfer element cycles the temperature in the entire defined section of the channel. That is, a constant temperature zone is used to provide the thermal cycling. In a further embodiment, an appropriately programmed computer controls the temperature cycling of the thermal transfer element. In one embodiment, the temperature of the thermal transfer element is detected and fed back to the computer. In accordance with these embodiments, heating and cooling are applied to a length of the channel (the reaction zone) such that its temperature follows a PCR profile in time. The test boluses are pumped through this reaction zone at a flow rate (speed) such that the number of PCR cycles required is achieved during the time the bolus flows from the upstream end to the downstream end of the reaction zone.

In another embodiment, the intensity of the fluorescent signal is measured at a specific time and/or temperature during the PCR temperature cycle. In an additional embodiment, the intensity of the fluorescent signal is measured once during each PCR cycle. In a further embodiment, the plurality of locations at which the intensity of the fluorescent signal is measured is the entire defined section of the channel. In another embodiment, the data concerning the intensity of the fluorescent signal is processed by an appropriately programmed computer. In another embodiment, an image of at least one fluorescent signal along the length of the channel is made. In a further embodiment, the image capture is performed repeatedly on consecutive temperature cycling periods. The image may be created or the intensity of the fluorescent signal measured using a multiple-pixel array detector. A stationary mechanism or a scanning mechanism or both may be used to capture the image.

In a second embodiment of the methods in accordance with the present invention, the performance of real-time PCR includes monitoring the flow rate (flow speed) of the fluid in the microchannel. The liquid may be the test solution or the carrier fluid. By monitoring the flow rate in the channel, the location of a test bolus as a function of time can be determined, thus identifying the number of PCR cycles that has been experienced by the test bolus. Thus, in accordance with this embodiment, a method for performing real-time PCR comprises the steps of: a) continuously moving a bolus of test solution containing real-time PCR reagents in a channel; b) moving a carrier-fluid in the channel, sequentially alternating with a test bolus; c) cycling the temperature in a defined section of the channel in order to achieve PCR; d) measuring the intensity of the fluorescent signal at a plurality of locations along the defined section of the channel and e) measuring the average flow rate of the fluid in the channel.

In one embodiment, average flow speed of the fluid is measured by comparing sequential images of the reaction-dependent fluorescent signal from the channel. In a second embodiment, the average flow speed of the fluid is measured by comparing sequential images of a marker (i.e., a reaction-independent marker) in the channel. The use of the marker has the advantage that if the real-time PCR signal is not detectable, the fluid flow would still be detectable. Examples of potential markers are dyes, semiconductor quantum dots, polymer microbeads, scattering metal particles, microbubbles, and the like known to skilled artisans. In one embodiment, the marker is present in the test solution. If the marker is present in the test solution, it should not adversely affect any PCR chemical reactions. In another embodiment, the marker is present in the carrier fluid. In a further embodiment, the marker is a separate bolus in series with test boluses. In an additional embodiment, the marker is resolvable from the fluorescent signal, such as by excitation wavelength, emission spectrum, lifetime, and the like well known in the art. In a further embodiment, the data concerning the sequential images of the intensity of the fluorescent signal or of the marker is processed by an appropriately programmed computer. In accordance with these embodiments, the average flow speed is determined by comparing images taken from consecutive PCR cycles. In a still further embodiment, the flow rate can be measured using a reaction zone entrance detector and a flow speed meter. Flow speed could be estimated, for example, by knowing the dimensions of the channel and measuring the volume flow rate.

In a third embodiment of the methods in accordance with the present invention, the performance of real-time PCR includes monitoring the flow rate (flow speed) of the fluid in the microchannel and adjusting the flow rate as necessary to control the duration of the PCR cycling experienced by a test solution. Thus, in accordance with this embodiment, a method for performing real-time PCR comprises the steps of: a) continuously moving a bolus of test solution containing real-time PCR reagents in a channel; b) moving a carrier-fluid in the channel, sequentially alternating with a test bolus; c) cycling the temperature in a defined section of the channel in order to achieve PCR; d) measuring the intensity of the fluorescent signal at a plurality of locations along the defined section of the channel; e) measuring the average flow speed of the fluid in the channel; and f) adjusting the flow rate of the fluid to control the duration of the PCR cycling.

In one embodiment, the flow rate is monitored and adjusted such that the desired number of PCR cycles is completed while the test solution is moving through the defined section of the channel. That is, the flow rate is adjusted to determine the duration of the PCR cycling. In another embodiment, this monitoring and adjustment is performed by an appropriately programmed computer, such as main control and processing computer 105. In a further embodiment, the flow rate is adjusted by regulating the pressure at the input end of the channel. In an additional embodiment, the flow rate is adjusted by regulating the pressure regulated vacuum at the output end of the channel. In another embodiment, the flow rate is adjusted by regulating a pump, such as a syringe pump. In one embodiment, the flow rate is monitored and adjusted so that the desired number of PCR cycles is performed as the test solution moves through the reaction zone of the microchannel. For example, if the reaction zone of the microchannel is 30 mm and it is desired to perform 30 PCR cycles, then the flow rate is monitored so that a flow rate of 1 mm/cycle is achieved and maintained. Since each PCR cycle may be on the order of 30-60 seconds, the flow speed in the microchannel is fairly slow in this example.

Figure 7:
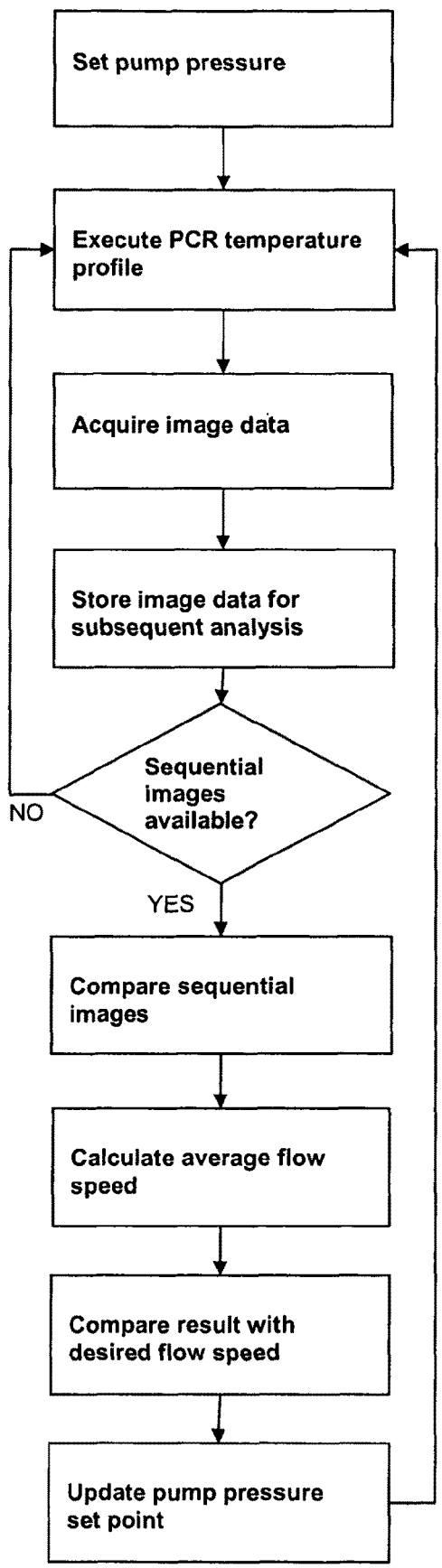
FIG. 7 shows a process diagram illustrating a mode of operation according to one embodiment of the invention.

FIG. 7 is a process diagram illustrating a mode of operation for regulating the flow speed of the fluid as moves through the channels according to one embodiment of the invention. In this embodiment, a closed loop feedback is used to regulate the flow speed. First, the fluid in the channels is moved by activating a regulated pressure pump, such as, for example, pump mechanism 106, at a pump pressure set point. As the fluid moves through the channel, a PCR temperature profile is executed over a defined section of a channel. At an appropriate time during the PCR temperature cycle, the system acquires one or more images of the contents of the channel. These image data and the time of acquisition are stored to a database for subsequent analysis, such as, for example, the main control and processing computer 105. If two sequential images are not available, the temperature cycling and image acquisition repeat without changing the pressure set point. If two sequential images are available, they may be compared to determine how far the fluid has moved along the channel. Dividing the average displacement by the time elapsed gives an average flow speed. If there is a difference between the measured flow speed and the desired flow speed, the pump pressure set point is adjusted automatically so that the desired flow speed obtained, and the process is repeated. If there is no difference between the measured flow speed and the desired flow speed, the pump pressure set point remains the same, and the process is repeated.

The above described systems are specifically adapted for methods for monitoring the progress of a polymerase chain reaction in a microchannel. In accordance with one embodiment, a method for monitoring the progress of a polymerase chain reaction in a microchannel comprises the steps of: a) moving a bolus of test solution containing real-time PCR reagents in a microchannel; b) moving a carrier fluid in said microchannel, sequentially alternating with a test bolus; c) cycling the temperature in a defined section of the microchannel in order to achieve PCR; d) capturing an image of a reaction-dependent fluorescence signal along a section of the microchannel; e) measuring the average flow rate in the microchannel; and f) relating position of the test bolus to the number of temperature cycles experienced by a test bolus from the average flow rate.

In one embodiment, the average flow rate is measured by comparing sequential images of the reaction-dependent fluorescent signal from the channel. In a second embodiment, the average flow rate is measured by comparing sequential images of a reaction-independent flow marker from the channel. The reaction-independent flow marker may be (i) premixed in the test bolus, (ii) introduced to the channel as a bolus alternating with the test bolus or (iii) pre-mixed in the carrier fluid. In another embodiment, scattered light from the reaction-independent flow marker is resolvable from the reaction-dependent fluorescence by wavelength spectrum. In an alternative embodiment, scattered light from the reaction-independent flow marker is resolvable from the reaction-dependent fluorescence on the basis of fluorescence lifetime. In another embodiment, the reaction-independent flow marker is further used to determine the flow dispersion of the test bolus. In a further embodiment, the image of reaction-dependent fluorescence is captured at least once per PCR cycle. In one embodiment, the image of reaction-dependent fluorescence is captured sequentially by scanning a length of the channel on a time scale shorter than the duration of one PCR cycle. In an alternative embodiment, the image of reaction-dependent fluorescence is captured by acquiring signal from multiple points along the channel simultaneously. In another embodiment, the flow rate measurements are part of a feedback loop for regulating the flow rate. In a further embodiment, the flow rate is measured through detecting a sample bolus entrance into and exit from a defined section of the channel.

In accordance with another embodiment, a method for monitoring the progress of a polymerase chain reaction in a microchannel comprises the steps of: a) moving a bolus of test solution containing real-time PCR reagents in a microchannel; b) moving a carrier fluid in the same microchannel, sequentially alternating with a test bolus; c) applying spatial temperature zones along the microchannel to achieve PCR; d) monitoring the fluorescence signal at fixed spatial locations along the microchannel corresponding to fixed points in the PCR cycle; e) measuring the average flow rate of the fluid in the microchannel; and f) adjusting the flow rate in order to control the timing of the PCR cycle.

In one embodiment, the temperature is cycled using a thermal transfer element along portions of the channel. In another embodiment, the thermal transfer element cycles the temperature in the portions of the channel. In a further embodiment, an appropriately programmed computer controls the temperature cycling of the thermal transfer element, such as main control and processing computer illustrated in FIG. 1. In one embodiment, the temperature of the thermal transfer element is detected and fed back to the computer. In accordance with these embodiments, heating and cooling are applied to portions of the channel such that a PCR temperature profile is followed. The test boluses are pumped through this reaction zone at a flow rate (speed) such that the number of PCR cycles required is achieved during the time the bolus flows from the upstream end to the downstream end of the reaction zone. By monitoring the flow rate in the channel in this aspect of the invention, the duration of the PCR cycle period can be determined.

In one embodiment, the present invention also provides systems and/or kits adapted for practicing the above described methods. As illustrated above, the systems and/or kits can include system instructions (e.g., embodied in a computer or in a computer readable medium, e.g., as system software) for practicing any of the method steps herein. Fluid handling elements for storing, transferring, aliquotting, or diluting samples, e.g., microfluidic handling elements, and detector elements can also be components of the systems and kits herein. In addition, packaging materials, integration elements (e.g., instrument cases, power supplies, etc.), instructions for using the systems and kits and the like can be features of the invention.

In one embodiment, the invention provides a system that includes a microfluidic device comprising one or more amplification channels (microchannels) each configured to thermocycle one or more test solutions. A thermal transfer element for cycling the temperature along a defined section of the channel(s) is also included. The thermal transfer element is integral with or proximal to the microfluidic device. A source of illumination integral with or proximal to the microfluidic device is also included, where the source of illumination is configured to illuminate the channel(s). A detector integral with or proximal to the microfluidic device is also included, where the detector is configured to detect the amplification products and/or marker in the channel(s). In one embodiment, the detector can independently detect signals from two or more detectable markers with different signals; e.g., a detector that can simultaneously detect fluorescent or other emissions at two or more frequencies, such as the system illustrated in FIG. 6. The system includes one or more elements for controlling the flow rate of the continuously moving test solution and carrier fluid in the channel(s), as well as system instruction or software for monitoring and controlling the flow rate in order to control the timing of each PCR cycle. Typically, the system includes a sensor to detect the temperature of the thermal transfer element and to provide feedback information for controlling the temperature cycles. Typically, the system also includes system software for generating and processing data, such as timing the detection of the amplified products and/or marker, monitoring location of test solutions in the channel(s) and the like.

In one embodiment, the system may also include a dilution module that dilutes the sample into multiple test solutions, as well as system instructions that direct the dilution module to aliquot the sample into a plurality of test solutions. The dilution module may be integral with or proximal to the microfluidic device.

In one embodiment, the system optionally comprises software with instructions for performing any of the method steps described herein. For example, the system can include statistical or probabilistic system software that performs one or more statistical or probabilistic analysis of signals received from one or more of the test solutions subjected to thermocycling. For example, the statistical or probabilistic analysis can include Poisson analysis, Monte Carlo analysis, application of a genetic algorithm, neural network training, Markov modeling, hidden Markov modeling, multidimensional scaling, partial least square (PLS) analysis, and/or principle component analysis (PCA). The statistical or probabilistic analysis optionally comprises quantitatively determining a concentration, proportion, or number of the nucleic acids of interest in the sample. These statistical evaluations can be used to correlate abundance or proportions to diagnosis or prognosis associated with the diagnosis or prognosis.

In one embodiment, the system also optionally includes fluid handling or storage features such as sample storage modules that store the samples until they are to be diluted by the dilution module, a sample retrieval module that retrieves the sample from the sample storage module and delivers it to the dilution module, or the like. These features are optionally designed to provide for continuous flow of fluid (e.g., comprising the sample) through the system (thereby providing for higher sample throughput). The system may also include means and system software for analyzing the amplified product. In one embodiment, the system may include system software that correlates a reproducible signal shape, length, width, volume or area occupied by the amplification products, as detected by the detector, to (a) the number of copies of the nucleic acid of interest present in one of the test solutions, or to the number of copies of the nucleic acid of interest present in the sample, or both or (b) an identification of the amplification product(s) present in the sample or (c) any other analytical parameters known and used in the art.

The nucleic acid of interest that can be amplified and detected in the methods of the invention can be essentially any nucleic acid. The sequences for many nucleic acids and amino acids (from which nucleic acid sequences can be derived via reverse translation) are available. No attempt is made to identify the hundreds of thousands of known nucleic acids, any of which can be detected in the methods of the invention. Common sequence repositories for known nucleic acids include GenBank EMBL, DDBJ and the NCBI. Other repositories can easily be identified by searching the internet. The nucleic acid can be an RNA (e.g., where amplification includes RT-PCR) or DNA (e.g., where amplification includes PCR), or an analogue thereof (e.g., for detection of synthetic nucleic acids or analogues thereof). Any variation in a nucleic acid can be detected, e.g., a mutation, a single nucleotide polymorphism (SNP), an allele, an isotype, a fragment, a full-length nucleic acid, an amplicon, etc. Further, because the present invention is quantitative, one can detect variations in expression levels, fragmentation, or gene copy numbers by the methods.

In general, the methods of the invention are particularly useful in screening samples derived from patients for the nucleic acids of interest, e.g., from bodily fluids and/or waste from the patient. This is because samples derived from relatively large volumes of such materials can be screened in the methods of the invention (removal of such materials is also relatively non-invasive). The nucleic acids of interest (e.g., present in cancer cells) can easily comprise 1% or less of the related nucleic acid population of the sample (e.g., about 1%, 0.1%, 0.001%, 0.0001% or less of the alleles for a gene of interest). Thus, whole blood, serum, plasma, stool, urine, vaginal secretions, ejaculatory fluid, synovial fluid, a biopsy, cerebrospinal fluid, and amniotic fluid, sputum, saliva, lymph, tears, sweat, or urine, or the like, can easily be screened for rare nucleic acids or fragmentation by the methods of the invention, as can essentially any tissue of interest. These samples are typically taken, following informed consent, from a patient by standard medical laboratory methods.

Prior to amplification, nucleic acids are optionally purified from the samples by any available method, e.g., those taught in Berger and Kimmel (*Methods in Enzymology* 152, Academic Press, Inc., San Diego, Calif., 1987); Sambrook and Russell, *Molecular Cloning*, 3rd Ed. (Cold Spring Harbor Laboratory Press, Cold Spring Harbor, N.Y., 2001); Ausubel et al., *Current Protocols in Molecular Biology* (John Wiley & Sons, updated through 2005). A plethora of kits are also commercially available for the purification of nucleic acids from cells or other samples (see, e.g., EasyPrep™, Flex-iPrep™, both from Pharmacia Biotech; StrataClean™ from Stratagene; and, QIAprep™ from Qiagen). Alternately, samples can simply be directly subjected to amplification, e.g., following aliquoting and dilution. One advantage of single molecule detection is that the low concentration of sample components in the reaction can reduce the need for nucleic acid purification. That is, dilution of the sample reduces the abundance of unwanted components at the same time it distributes the nucleic acid of interest into reaction mixtures.

One class of nucleic acids of interest to be detected in the methods herein is those involved in cancer. Any nucleic acid that is associated with cancer can be detected in the methods of the invention, e.g., those that encode over expressed or mutated polypeptide growth factors (e.g., sis), over expressed or mutated growth factor receptors (e.g., erb-B1), over expressed or mutated signal transduction proteins such as G-proteins (e.g., Ras), or non-receptor tyrosine kinases (e.g., abl), or over expressed or mutated regulatory proteins (e.g., myc, myb, jun, fos, etc.) and/or the like. In a preferred embodiment, specific or arbitrary nucleic acids of interest are screened for the amount of fragmentation, with high fragmentation generally associated with apoptosis of normal cells and less fragmentation associated, e.g., with sloughing of cancer cells. In general, cancer can often be linked to signal transduction molecules and corresponding oncogene products, e.g., nucleic acids encoding Mos, Ras, Raf, and Met; and transcriptional activators and suppressors, e.g., p53, Tat, Fos, Myc, Jun, Myb, Rel, and/or nuclear receptors. p53, colloquially referred to as the "molecular policeman" of the cell, is of particular relevance, as about 50% of all known cancers can be traced to one or more genetic lesion in p53.

One class of genes that are relevant to cancer is the class of nuclear hormone receptors, which have been described in detail and the mechanisms by which these receptors can be modified to confer oncogenic activity have been worked out. For example, the physiological and molecular basis of thyroid hormone action is reviewed in Yen (*Physiological Reviews* 81:1097-1142, 2001), and the references cited therein. Known and well characterized nuclear receptors include those for glucocorticoids (GRs), androgens (ARs), mineralocorticoids (MRs), progestins (PRs), estrogens (ERs), thyroid hormones (TRs), vitamin D (VDRs), retinoids (RARs and RXRs), and the peroxisome proliferator activated receptors (PPARs) that bind eicosanoids. The so called "orphan nuclear receptors" are also part of the nuclear receptor superfamily, and are structurally homologous to classic nuclear receptors, such as steroid and thyroid receptors. Nucleic acids that encode any of these receptors, or oncogenic forms thereof, can be detected in the methods of the invention. About 40% of all pharmaceutical treatments currently available are agonists or antagonists of nuclear receptors and/or oncogenic forms thereof, underscoring the relative importance of these receptors (and their coding nucleic acids) as targets for analysis.

One class of nucleic acids of interest involved with cancer are those that are diagnostic of colon cancer, e.g., in samples derived from stool. Colon cancer is a common disease that can be sporadic or inherited. The molecular basis of various patterns of colon cancer is known in some detail. In general, germline mutations are the basis of inherited colon cancer syndromes, while an accumulation of somatic mutations is the basis of sporadic colon cancer. In Ashkenazi Jews, a mutation that was previously thought to be a polymorphism may cause familial colon cancer. Mutations of at least three different classes of genes have been described in colon cancer etiology: oncogenes, suppressor genes, and mismatch repair genes. One example nucleic acid encodes DCC (deleted in colon cancer), a cell adhesion molecule with homology to fibronectin. An additional form of colon cancer is an autosomal dominant gene, hMSH2 that comprises a lesion. Familial adenomatous polyposis is another form of colon cancer with a lesion in the MCC locus on chromosome #5. For additional details on Colon Cancer, see, Calvert et al. (*Annals of Internal Medicine* 137:603-612, 2002) and the references cited therein. For a variety of colon cancers and colon cancer markers that can be detected in stool, see, e.g., Boland (*Reviews In Gastroenterological Disorders* 2 Supp. 1:S12-S19, 2002) and the references cited therein. As with other cancers, mutations in a variety of other genes that correlate with cancer, such as Ras and p53, are useful diagnostic indicators for cancer. In another aspect, detection of fragmentation levels using methods of the present invention can be particularly useful in detection of colon cancer. For example, as the amount of total patient DNA available in a stool specimen is low, the amplification aspect of the present invention can be beneficial to examination of the DNA. Whereas the DNA from cells sloughed from the normal colon lining is generally degraded into fragments, e.g., of about 100 base pairs in length, DNA entering the colon lumen from a colon tumor cells can remain generally unfragmented. Detecting the presence of a proportion of unfragmented nucleic acids over a certain threshold in a stool specimen can correlate to presence of a colon cancer.

Cervical cancer is another target for detection, e.g., in samples obtained from vaginal secretions. Cervical cancer can be caused by the human papilloma virus and has two oncogenes, E6 and E7. E6 binds to and removes p53 and E7 binds to and removes PRB. The loss of p53 and uncontrolled action of E2F/DP growth factors without the regulation of pRB is one mechanism that leads to cervical cancer. Furthermore, as with colon cancer, detecting the presence of a proportion of unfragmented nucleic acids over a certain threshold in a vaginal swab can correlate to the presence of a cervical cancer.

Other targets for detection by the methods of the invention include retinoblastoma, e.g., in samples derived from tears, and Neurofibromatosis Type 1, e.g. in CSF or via tissue sampling. Many other forms of cancer are known and can be found by detecting, e.g., associated genetic lesions, fragmentation proportions, or absolute concentrations of full-length nucleic acids of interest using the methods of the invention. Cancers that can be detected by detecting appropriate lesions or fragmentation values include cancers of the lymph, blood, stomach, gut, colon, testicles, pancreas, bladder, cervix, uterus, skin, and essentially all others for which an associated genetic lesion or fragmentation threshold exists. For a review of the topic, see, *The Molecular Basis of Human Cancer*, Coleman and Tsongalis (Eds), Humana Press, Totowa, N.J., 2001).

Similarly, nucleic acids from pathogenic or infectious organisms can be detected by the methods of the invention, e.g., for infectious fungi, e.g., *Aspergillus*, or *Candida* species; bacteria, particularly *E. coli*, which serves a model for pathogenic bacteria (and, of course certain strains of which are pathogenic), as well as medically important bacteria such as Staphylococci (e.g., aureus), or Streptococci (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B. Single and low copy amplification methods of the invention can be useful in many cases, e.g., in exudates from bacterial infections to identify living (having full length nucleic acids) versus dead and lysed pathogens (having fragmented nucleic acids).

A variety of nucleic acid encoding enzymes (e.g., industrial enzymes) can also be detected according to the methods herein, such as amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases. Similarly, agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., ribulose 1,5-bisphosphate carboxylase/oxygenase), lipoxygenase (LOX), and phosphoenolpyruvate (PEP) carboxylase can also be detected.

The sample can be aliquotted and/or diluted using standard or microfluidic fluid handling approaches (or combinations thereof). Standard fluid handling approaches for dilution/aliquotting include, e.g., pipetting appropriate volumes of the sample into microtiter trays and adding an appropriate diluent. These operations can be performed manually or using available high throughput fluid handlers, such as, e.g., those designed to use serially dilute solutions in microtiter trays. High throughput equipment (e.g., incorporating automated pipettors and robotic microtiter tray handling) is preferred, as the present invention contemplates making and using high numbers of aliquots of a sample of interest.

Many automated systems for fluid handling are commercially available and can be used for aliquotting and/or diluting a sample in the context of the present invention. For example, a variety of automated systems are available from the Zymark Corporation (now Caliper Life Sciences, Hopkinton, Mass.), which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). In any case, a conventional high throughput systems can be used in place of, or in conjunction with microfluidic systems (for example, conventional systems can be used to aliquot samples into microtiter trays, from which microfluidic systems can draw materials) in practicing the methods of the invention.

Microfluidic systems provide a preferred fluid handling and amplification technology that can conveniently be applied to the present invention. In typical embodiments, such as those described above, samples are drawn into microfluidic devices that comprise networks of microscale cavities (channels, chambers, etc., having at least one dimension less than about 500 μM in size and often less than about 100 μM) and the samples are mixed, diluted, aliquotted or otherwise manipulated in the network of cavities (e.g., channels and/or chambers). For example, the microscale device can comprise one or more capillary, in fluid communication with the network, extending outward from a body structure of the microscale device. In one embodiment, negative pressure (vacuum) is applied to the capillary and fluids are drawn into the network from a container (e.g., a well on a microtiter tray). This process can be multiplexed by using a device that comprises multiple capillary channels, permitting many samples to be drawn into the network and processed simultaneously. Alternately, multiple samples can be sequentially drawn into the microfluidic device and routed internally to multiple channels for simultaneous processing and analysis. Sample interfaces with dried samples can also be performed using this basic system, e.g., by partly or completely expelling fluid from the capillary to hydrate samples prior to drawing them into the microfluidic device (the fluid is typically contacted to the samples as a hanging drop on the tip of the capillary and then drawn back into the capillary). For either approach, see also, U.S. Pat. Nos. 6,482,364, 6,042,709, 6,287,520 and 6,235,471. Essentially any fluid manipulation (aliquotting, diluting, heating and cooling) can be performed in the network using available methods. Details regarding dilution and aliquotting operations in microscale devices can be found in the patent literature, e.g., U.S. Pat. Nos. 6,149,870, 5,869,004 and 6,440,722. Samples and components to be mixed/diluted or aliquotted can be brought into the microscale device through pipettor elements or from reaction component reservoirs on the device itself, or, commonly, both. For example, the sample can be brought into the microfluidic device through a pipettor channel and diluted and supplied with common reagents from an on device dilution and/or reagent reservoir(s). Locus specific reagents (e.g., amplification primer pairs) can be on the device in wells, or stored off the device, e.g., in microtiter plates (in which case they can be accessed by the pipettor channel). Any or all of these operations can be performed in a continuous or stopped flow format.

The microfluidic device typically performs several functions, including reaction assembly (assembly of reaction mixtures), thermocycling, and acting as a "cuvette" for an optical system during an imaging (detection) step. In the reaction assembly, the reaction mixture components (particularly magnesium and the enzyme) which get combined at the last second before heating begins are assembled. This is called a "hot start" and provides advantages of specificity. During thermocycling, the system optionally provides both constant fluid movement and a continuous sequence of temperature changes. During imaging, a high data rate CCD detector, a multiple-pixel array detector or a fiber-optic ball head lens detector, for example, is useful in providing an adequate dynamic range for methods of quantification.

Commercial systems that perform all aspects of fluid handling that can be used in the practice of the present invention are available. Examples include the 250 HTS system and AMS 90 SE from Caliper Life Sciences (Hopkinton, Mass.). These systems perform experiments in serial, continuous flow fashion and employ a "chip-to-world" interface, or sample access system, called a sipper through which materials in microwell plates are sipped into a capillary or capillaries attached to the chip and drawn into the channels of the chip. There they are mixed with components of interest and a processing and result detection steps are performed. See, for example, U.S. Published Patent Application No. 2005/0042839.

Whether conventional fluid handling or microfluidic approaches (or both) are used, the aliquotting and/or dilution events can be performed to achieve particular results. For example, a sample can be diluted equally in each aliquot, or, alternately, the aliquots can be differentially diluted (e.g., a dilution series can be made). The aliquots themselves can be of a volume that is appropriate to the fluid handling approach being used by the system, e.g., on the order of a few microliters for microtiter plates to 100 mL, 10 mL or even 1 mL or less for microfluidic approaches.

The aliquots can be selected to have high or low copy numbers of any relevant nucleic acid (e.g., for low copy number aliquots, 50 or fewer, generally 25 or fewer, usually 10 or fewer and often 5 or fewer, 2 or fewer or 1 or fewer copies of the relevant nucleic acid(s)). The number of aliquots generated will depend on the size of the sample and the amount of quantitative information desired by the practitioner. For example, where simple detection of a rare nucleic acid is desired, enough low and/or single copy number aliquots are made of the sample to detect the nucleic acid in one of the aliquots. Where more quantitative information is needed, enough copies are made to provide reliable statistical information, e.g., to a given confidence value. In either case, this can include anywhere from 1 aliquot to $10^9$ or more aliquots, e.g., 10, 100, 1,000, 10,000, 100,000, 1,000,000, 1,000,000,000 or more aliquots. There is no theoretical limit on the number of aliquots that can be made and assessed for a nucleic acid of interest according to the present invention, though there are practical considerations with respect to the throughput of the system and the size of the sample (the lower the throughput, the fewer aliquots can be analyzed in a given time; the larger the sample size the more aliquots can be made of the sample). Using microfluidic approaches, reagent usage (and concomitant reagent costs) can be minimized. By formatting the system to provide for continuous flow of sample and reagents, including, optionally, during amplification, the systems of the invention can greatly speed the process of searching many different samples for a nucleic acid of interest. Similarly, if stopped flow approaches are used, simultaneous processing of signals from PCR reactions can be used to speed the process of searching samples for a nucleic acid of interest. In the examples below, about 150 aliquots for each dilution range was sufficient to provide reasonable quantitative information for Poisson statistics for model samples. Obviously, more or fewer aliquots can be used in the methods as well.

The methods of the invention include amplifying one or more sequences of a nucleic acid of interest from a sample or aliquot and, optionally, one or more additional nucleic acids. Real time PCR and/or real time reverse transcriptase-PCR (e.g., mediated via TaqMan® probes, molecular beacon-based probes or quantum dot based probes) are used to facilitate detection of amplified nucleic acids.

It is expected that one of skill is generally familiar with the details of these amplification methods. Details regarding these amplification methods can be found, e.g., in Sambrook and Russell, *Molecular Cloning,* 3rd Ed. (Cold Spring Harbor Laboratory Press, Cold Spring Harbor, N.Y., 2001); Ausubel et al., *Current Protocols in Molecular Biology* (John Wiley & Sons, New York, updated through 2005); *Real-Time PCR: An Essential Guide,* K. Edwards et al., eds. (Horizon Bioscience, Norwich, U.K., 2004).

In one aspect, real time PCR is performed on the various aliquots or reaction mixtures such as described herein, e.g., using fluorescent labels. It will be recognized that fluorescent labels are not to be limited to single species organic molecules, but include inorganic molecules, multi-molecular mixtures of organic and/or inorganic molecules, crystals, heteropolymers, and the like. Suitable fluorescent labels can be provided by, e.g., DNA binding dyes, molecular beacons, TaqMan® probes or quantum dots. The amplification product (which is double stranded) binds dye molecules in solution to form a complex. With the appropriate dyes, it is possible to distinguish between dye molecules free in solution and dye molecules bound to amplification product. For example, certain dyes fluoresce only when bound to amplification product. Examples of suitable dyes include, but are not limited to, LC Green (Idaho Technology, Salt Lake City, Utah), SYBR® Green, SYBR® GreenER™ and Pico Green (Invitrogen Corp., Carlsbad, Calif.), ethidium bromide, propidium iodide, chromomycin, acridine orange, Hoechst 33258, Hoechst 33342, Toto-1, Yoyo-1, and DAPI (4',6-diamidino-2-phenylindole hydrochloride). Additional discussion regarding the use of intercalation dyes is provided by Zhu et al. (*Anal Chem* 66:1941-1948, 1994).

A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched.

Details regarding standard methods of making and using MBs are well established in the literature and MBs are available from a number of commercial reagent sources. See also, e.g., Leone et al. (*Nucl Acids Res* 26:2150-2155, 1995); Tyagi and Kramer (*Nat Biotechnology* 14:303-308, 1996); Blok and Kramer (*Mol Cell Probes* 11:187-194, 1997); Hsuih et al. (*J Clin Microbiol* 34:501-507, 1997); Kostrikis et al. (*Science* 279:1228-1229, 1998); Sokol et al. (*Proc Natl Acad. Sci. USA* 95:11538-11543, 1998); Tyagi et al. (*Nat Biotechnology* 16:49-53, 1998; Bonnet et al. (*Proc Natl Acad Sci USA* 96:6171-6176, 1999); Fang et al. (*J Am Chem Soc* 121:2921-2922, 1999); Marras et al. (*Genet Anal Biomol Eng* 14:151-156, 1999); and Vet et al. (*Proc Natl Acad Sci USA* 96:6394-6399, 1999). Additional details regarding MB construction and use is found in the patent literature, e.g., U.S. Pat. Nos. 5,925,517, 6,150,097 and 6,037,130.

MBs are robust reagents for detecting and quantifying nucleic acids, including in real time, e.g., during PCR, LCR or other nucleic acid amplification reactions (e.g., MBs can be used to detect targets as they are formed). A variety of commercial suppliers produce standard and custom molecular beacons, including Cruachem (cruachem.com), Oswel Research Products Ltd. (UK; oswel.com), Invitrogen Corp. (Carlsbad, Calif.; invitrogen.com), the Midland Certified Reagent Company (Midland, Tex. mcrc.com) and Gorilla Genomics, LLC (Alameda, Calif.). A variety of kits which utilize molecular beacons are also commercially available, such as the Sentinel™. Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com).

MB components (e.g., oligos, including those labeled with fluorophores or quenchers) can be synthesized using conventional methods. For example, oligos or peptide nucleic acids (PNAs) can be synthesized on commercially available automated oligonucleotide/PNA synthesis machines using standard methods. Labels can be attached to the oligos or PNAs either during automated synthesis or by post-synthetic reactions which have been described before see, e.g., Tyagi and Kramer (*Nat Biotechnology* 14:303-308, 1996) and U.S. Pat. Nos. 6,037,130 and 5,925,517. Additional details on synthesis of functionalized oligos can be found in Nelson et al. *Nucl Acids Res* 17:7187-7194, 1989). Labels/quenchers can be introduced to the oligonucleotides or PNAs, e.g., by using a controlled-pore glass column to introduce, e.g., the quencher (e.g., a 4-dimethylaminoazobenzene-4'-sulfonyl moiety (DABSYL). For example, the quencher can be added at the 3' end of oligonucleotides during automated synthesis; a succinimidyl ester of 4-(4'-dimethylaminophenylazo)benzoic acid (DABCYL) can be used when the site of attachment is a primary amino group; and 4-dimethylaminophenylazo-phenyl-4'-maleimide (DABMI) can be used when the site of attachment is a sulphydryl group. Similarly, fluorescein can be introduced in the oligos, either using a fluorescein phosphoramadite that replaces a nucleoside with fluorescein, or by using a fluorescein dT phosphoramadite that introduces a fluorescein moiety at a thymidine ring via a spacer. To link a fluorescein moiety to a terminal location, iodoacetoamidofluorescein can be coupled to a sulphydryl group. Tetrachlorofluorescein (TET) can be introduced during automated synthesis using a 5'-tetrachloro-fluorescein phosphoramadite. Other reactive fluorophore derivatives and their respective sites of attachment include the succinimidyl ester of 5-carboxyrhodamine-6G (RHD) coupled to an amino group; an iodoacetamide of tetramethylrhodamine coupled to a sulphydryl group; an isothiocyanate of tetramethylrhodamine coupled to an amino group; or a sulfonylchloride of Texas red coupled to a sulphydryl group. During the synthesis of these labeled components, conjugated oligonucleotides or PNAs can be purified, if desired, e.g., by high pressure liquid chromatography or other methods.

TaqMan® probes are composed of short (e.g., 20-25 bases) oligodeoxynucleotides that are labeled with two different fluorescent dyes. On the 5' terminus of each probe is a reporter dye, and on the 3' terminus of each probe a quenching dye is found. The oligonucleotide probe sequence can be complementary to an internal target sequence present in a PCR amplicon. When the probe is intact, energy transfer occurs between the two fluorophores and emission from the reporter is quenched by the quencher (fluorescent resonant energy transfer or FRET). During the extension phase of PCR, the probe is cleaved by 5' nuclease activity of the polymerase used in the reaction, thereby releasing the reporter from the oligonucleotide-quencher and producing an increase in reporter emission intensity.

Accordingly, TaqMan® probes are oligonucleotides that have a label and a quencher, where the label is released after hybridization and during amplification by the exonuclease action of the polymerase used in amplification. This provides a real time measure of amplification during synthesis. A variety of TaqMan® reagents are commercially available, e.g., from Applied Biosystems (Division Headquarters in Foster City, Calif.) as well as from a variety of specialty vendors such as Biosearch Technologies (e.g., black hole quencher probes).

A quantum dot is a fluorescent semiconductor nanocrystal having a characteristic spectral emission, which is tunable to a desired energy by selection of the particle size of the quantum dot. The quantum dot emits a characteristic emission spectrum which can be observed and measured spectrophotometrically. The emission spectra of quantum dots have linewidths as narrow as 25-30 nm depending on the size heterogeneity of the sample, and lineshapes that are symmetric, gaussian or nearly gaussian with an absence of a tailing region. The combination of tunability, narrow linewidths, and symmetric emission spectra without a tailing region provides for high resolution of multiply-sized quantum dots within a system and enables researchers to examine simultaneously a variety of biological moieties tagged with quantum dots. In addition, the range of excitation wavelengths of the nanocrystal quantum dots is broad and can be higher in energy than the emission wavelengths of all available quantum dots. Consequently, this allows the simultaneous excitation of all quantum dots in a system with a single light source, usually in the ultraviolet or blue region of the spectrum. Quantum dots are also more robust than conventional organic fluorescent dyes and are more resistant to photobleaching than the organic dyes. The use of quantum dots as fluorescent labels of nucleotides is described in Bruchez et al. (*Science* 281:2013-2016, 1998), Warren and Nie (*Science* 281:2016-2018, 1998), Alivisatos (*Science* 271:933-937, 1999) and U.S. Pat. Nos. 6,544,732 and 6,855,551. A variety of quantum dot reagents are commercially available, e.g., from Invitrogen Corp. (Carlsbad, Calif.; invitrogen.com) or Evident Technologies (Troy, N.Y., evidenttech.com).

Multicolor, multiplexed assays are a particular strength of quantum dot bioconjugates. The emission from quantum dot nanocrystals is narrow and symmetric; therefore, overlap with other colors is minimal, yielding less bleed through into adjacent detection channels and attenuated crosstalk and allowing many more colors to be used simultaneously. Since each bioconjugate color is based upon the same underlying material (they differ only in size), the conjugation and use methods for one color are easily extrapolated to all of the different colors, simplifying and speeding assay development. Furthermore, every quantum dot nanocrystal can be excited using a single light source—narrow laser and broad lamp excitation are both useful. Three- or four-color detection no longer requires multiple lasers or laborious alignments and compensations.

In general, synthetic methods for making oligonucleotides, including probes, molecular beacons, PNAs, LNAs (locked nucleic acids), etc., are well known. For example, oligonucleotides can be synthesized chemically according to the solid phase phosphoramidite triester method described by Beaucage and Caruthers (*Tetrahedron Letts* 22:1859-1862, 1981), e.g., using a commercially available automated synthesizer, e.g., as described in Needham-VanDevanter et al. (*Nucl Acids Res* 12:6159-6168, 1984). Oligonucleotides, including modified oligonucleotides can also be ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others. Similarly, PNAs can be custom ordered from any of a variety of sources, such as PeptidoGenic (pkim@ccnet.com), HTI Bioproducts, inc. (www.htibio.com), BMA Biomedicals Ltd (U.K.), Bio-Synthesis, Inc., and many others.

A number of high throughput approaches to performing PCR and other amplification reactions have been developed, e.g., involving amplification reactions in microfluidic devices, as well as methods for detecting and analyzing amplified nucleic acids in or on the devices. These high throughput approaches can be adapted for use with the present invention. Details regarding such technology is found, e.g., in the technical and patent literature, e.g., Kopp et al. (*Science* 280:1046-1048, 1998), Chow et al. (Science 282: 396-399, 1998), Zhang et al. (*Anal Chem* 71:1138-1145, 1999), U.S. Pat. Nos. 6,444,461, 6,406,893, 6,391,622, 6,303,343, 6,171,850, 5,939,291, to 5,955,029, 5,965,410 and 7,015,030, U.S. Published Patent Application Nos. 2004/0180346 and 2005/0042639, and many others.

Any available method for detecting amplified nucleic acids can be used in the present invention. Common approaches include real time amplification detection with molecular beacons, quantum dots or TaqMan® probes, detection of intercalating dyes (such as those described above), detection of labels incorporated into the amplified nucleic acids themselves and the like. Amplified nucleic acids (amplicons) can be detected in homogenous (substantially unseparated) reaction mixtures or solutions.

Amplification and detection are commonly integrated in a system comprising a microfluidic device in the present invention. Available microfluidic systems that include detection features for detecting nucleic acids include the 250 HTS system and AMS 90 SE from Caliper Technologies (Mountain View, Calif.), as well as the Agilent 2100 bioanalyzer (Agilent, Palo Alto, Calif.). Additional details regarding systems that comprise detection (and separation/detection) capabilities are well described in the patent literature, e.g., the references described herein and in PCT Published Patent Application No. WO 98/00231.

In general, the devices herein optionally include signal detectors, e.g., which detect fluorescence, phosphorescence, radioactivity, pH, charge, absorbance, luminescence, temperature, magnetism or the like. Fluorescent detection is especially preferred and generally used for detection of amplified nucleic acids, particularly for real-time PCR amplification (however, downstream operations can be performed on amplicons, which can involve other detection methods, such as mass spectroscopy or size exclusion).

The detector(s) optionally monitor one or a plurality of signals from an amplification reaction and/or hybridization reaction. For example, the detector can monitor optical signals which correspond to "real time" amplification assay results. The detector can monitor a single type of signal, or, e.g., simultaneously monitor multiple different signals.

Example detectors include photomultiplier tubes, photodiodes, avalanche photodiodes, photoresistors, bolometers, microchannel plate detectors, CCD arrays (including intensified and electron multiplying CCD arrays), CMOS image sensors, and/or the like. Wavelength discrimination may be achieved through the use of multilayer dielectric interference filters, color absorptive filters, or by dispersion with diffractive and/or refractive optical elements. Amplicons or other components which emit a detectable signal can be flowed past the detector, or, alternatively, the detector can move relative to the site of the amplification reaction (or, the detector can simultaneously monitor a number of spatial positions corresponding to channel regions, or microtiter wells e.g., as in a CCD array). Detectors in the present invention can detect signals from probes associated with nucleic acids of the invention that flow into one or more detection regions, e.g., of a microfluidic device.

The detector can include or be operably linked to a computer (or other logic device), e.g., which has software for converting detector signal information into assay result information (e.g., presence of a nucleic acid of interest, the length of a nucleic acid of interest, proportions of nucleic acid of interest lengths, and/or correlations with disease states), or the like.

Signals are optionally calibrated, e.g., by calibrating the microfluidic system by monitoring a signal from a known source. For example, signals can be calibrated against a reference light source, internal reference signals, or normalized for detection of positive signals over background.

A microfluidic system according to the present invention can also employ multiple different detection systems for monitoring signals in the system. Detection systems of the present invention are used to detect and monitor the materials in a particular channel region (or other reaction detection region). Once detected, the flow rate and velocity of any cells or droplets in the channels can be optionally measured by sensors and controlled as described above.

Examples of detection systems useful in methods and systems of the invention can include optical sensors, temperature sensors, pressure sensors, pH sensors, conductivity sensors, and the like. Each of these types of sensors is readily incorporated into the microfluidic systems described herein. In these systems, such detectors can be placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Preferred detection systems in accordance with the present invention include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally spectrophotometers, photodiodes, avalanche photodiodes, photomultiplier tubes, diode arrays, or in some cases, imaging systems, such as charged coupled devices (CCDs) and the like. The detection system is typically coupled to a computer, via an analog to digital or digital to analog converter, for transmitting detected light data to the computer for analysis, storage and data manipulation.

In the case of fluorescent materials such as labeled amplicons, the detector typically includes a light source that produces light at an appropriate wavelength for activating the fluorescent material, as well as optics for directing the light source through the detection window to the material contained in the channel or chamber. The light source can be any number of light sources that provides an appropriate wavelength, including lasers and LEDs. Other light sources are used in other detection systems. For example, broad band light sources are typically used in light scattering/transmissivity detection schemes, and the like. Typically, light selection parameters are well known to those of skill in the art.

The detector can exist as a separate unit, but can also be integrated with the system or microfluidic device, into a single instrument. Integration of these functions into a single unit facilitates connection of these instruments with the computer, by permitting the use of few or a single communication port(s) for transmitting information between the controller, the detector and the computer.

General references that are useful in understanding how to generate and analyze data, as well as other relevant concepts include: Weiss (*Introductory Statistics, 7th* Ed., Addison-Wesley, Reading, Mass., 2004); Weiss (*Elementary Statistics, 5th* Ed., Addison-Wesley, Reading, Mass., 2001); Berinstein (*Finding Statistics Online: How to Locate the Elusive Numbers You Need*, Information Today, Medford, N.J., 1998); Everitt, (*The Cambridge Dictionary of Statistics*, Cambridge University Press, New York, 1998); Kotz (*Encyclopedia of Statistical Sciences*, vol. 1-9 plus supplements, Wiley, New York, 1988); Dillon and Goldstein (*Multivariate Analysis: Methods and Applications*, Wiley, New York, 1984); Tabachnick and Fidell (*Using Multivariate Statistics*, HarperCollins College Publishers, New York, 1996); Box et al. (*Statistics for Experimenters*, Wiley, New York, 1978); Cornell (*Experiments with Mixtures*, Wiley, New York, 1990); John (*Statistical Design and Analysis of Experiments*, SIAM, Philadelphia, 1998); Gibas and Jambeck (*Bioinformatics Computer Skills*, O'Reilly, Sebastipol, Calif., 2001); Pevzner (*Computational Molecular Biology and Algorithmic Approach*, The MIT Press, Cambridge, Mass., 2000); Durbin et al. (*Biological Sequence Analysis: Probabilistic Models of Proteins and Nucleic Acids*, Cambridge University Press, Cambridge, UK, 1998); and Rashidi and Buehler (*Bioinformatic Basics: Applications in Biological Science and Medicine*, CRC Press LLC, Boca Raton, Fla., 2000).

The highly reproducible peak parameters, e.g., amplitude, width area, and/or shape features of a signal from an amplification reaction can be correlated to the starting copy number for the reaction and/or used to discriminate signals of interest from background fluctuations. This correlation can be performed at the theoretical level, taking thermal diffusivity and Taylor Aris dispersion into account, or it can be performed by comparison to standards (e.g., comparisons to peak shapes, e.g., heights, widths, or general shape profiles for amplification reactions that have known copy numbers for starting materials). The same or different peak parameters can be evaluated in interpretation of detector signals for two on more probes in determination of nucleic acid length.

For freely diffusing particles in a pressure-driven, laminar flow channel, the concentration profile along the channel may be approximated using a modified diffusion equation. See G. I. Taylor (*Proc Roy Soc Lond* A 219:186 (1953)) and R. Aris (*Proc Roy Soc Lond* A 235:67 (1956)). The Taylor dispersion coefficient ($D_T$) is dependent on the dimensions and shape of the microfluidic cavity through which the marker is flowed, the average flow velocity (v) and the molecular diffusivity ($D_m$). $D_T = D_m(1+k^2v^2w^2/D_m^2)$, where w is a characteristic channel width and k is a dimensionless factor that depends on the shape of the channel cross-section. Preferably, fluid parameters and channel dimensions are chosen to reduce dispersion to an acceptable level.

The systems of the invention can include microfluidic devices, reaction mixtures, detectors, sample storage elements (microtiter plates, dried arrays of components, etc.), flow controllers, amplification devices or microfluidic modules, computers and/or the like. These systems can be used for aliquotting, amplifying and analyzing the nucleic acids of interest. The microfluidic devices, amplification components, detectors and storage elements of the systems have already been described in some detail above. The following discussion describes appropriate controllers and computers, though many configurations are available and one of skill would be expected to be familiar in their use and would understand how they can be applied to the present invention.

A variety of controlling instrumentation is optionally utilized in conjunction with the microfluidic devices described herein, for controlling the transport and direction of fluids and/or materials within the devices of the present invention, e.g., by pressure-based or electrokinetic control.

For example, in many cases, fluid transport and direction are controlled in whole or in part, using pressure based flow systems that incorporate external or internal pressure sources to drive fluid flow. Internal sources include microfabricated pumps, e.g., diaphragm pumps, thermal pumps, Lamb wave pumps and the like that have been described in the art. See, e.g., U.S. Pat. Nos. 5,271,724, 5,277,556, and 5,375,979 and PCT Published Patent Application Nos. WO 94/05414 and WO 97/02357. The systems described herein can also utilize electrokinetic material direction and transport systems.

Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are described in U.S. Published Patent Application No. 2002/0019059.

Typically, the controller systems are appropriately configured to receive or interface with a microfluidic device or system element as described herein. For example, the controller and/or detector, optionally includes a stage upon which a microfluidic device is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also optionally used to provide for electrokinetic injection or withdrawal of material downstream of the region of interest to control an upstream flow rate. The same instrumentation and techniques described above are also utilized to inject a fluid into a downstream port to function as a flow control element.

As noted above, either or both of the controller system and/or the detection system can be coupled to an appropriately programmed processor or computer (logic device) which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed), such as the main control and processing computer 105 illustrated in FIG. 1.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates (including for continuous flow), temperatures, applied voltages, and the like.

The systems and/or kits can include system instructions (e.g., embodied in a computer or in a computer readable medium, e.g., as system software) for practicing any of the method steps herein. For example, the system optionally includes system software that correlates a shape, length, width, volume and/or area occupied by amplified copies of the nucleic acid of interest, as detected by the detector, to the number of copies of the nucleic acid of interest present in one of the aliquots, or to the number of copies of the nucleic acid of interest present in the sample, or both. Similarly, the system optionally includes system instructions that direct the dilution module to aliquot the sample into a plurality of aliquots, including a plurality of zero copy aliquots comprising no copies of the nucleic acids of interest and one or more single copy aliquot comprising a single copy of the nucleic acid of interest.

The statistical functions noted above can also be incorporated into system software, e.g., embodied in the computer, in computer memory or on computer readable media. For example, the computer can include statistical or probabilistic system software that performs one or more statistical or probabilistic analysis of signals received from one or more of the aliquots subjected to amplification (e.g., via thermocycling). The statistical or probabilistic analysis software optionally quantitatively determines a concentration, proportion, or number of the nucleic acids of interest in the sample.

Computers and software of the systems receive and evaluate signal data from one or more analyses to provide quantitation and/or proportionality determinations for nucleic acids of interest. In a basic form, e.g., the amplitude or integrated area of a signal can be adjusted with a conversion factor for an output in desired units, such as, e.g., copies per nL, ng/µL, and the like. Alternately, one or more standard materials of known concentration can be analyzed to provide data for regression analyses wherein changes in detectable signals with changes in concentration are expressed as an equation (standard curve) from which unknown concentrations can be determined by insertion of one or more signal parameters into the equation. In a particular embodiment, quantitation of a nucleic acid of interest can be based on the number of amplification cycles required to obtain a signal of a certain intensity.

In the present invention, the computer typically includes software for the monitoring of materials in the channels. Additionally, the software is optionally used to control electrokinetic or pressure modulated injection or withdrawal of material. The injection or withdrawal is used to modulate the flow rate as described above, to mix components, and the like.

The following example is offered to illustrate, but not to limit the claimed invention. It is understood that the example and embodiments described herein are for illustrative purposes only and that various modifications or changes in light thereof will be suggested to persons skilled in the art and are to be included within the spirit and purview of this application and scope of the appended claims.

An experiment was conducted to demonstrate the real-time detection of PCR amplification in a microfluidic device under continuous flow conditions. An 8 channel microfluidic device was used for this experiment. The dimensions of each microchannel were approximately 180 µm wide by 11 µm deep. The reaction zone of the microfluidic device was approximately 40 mm in length. fimA bacterial DNA was amplified using standard real-time PCR techniques. Test solution containing fimA DNA template and real-time PCR reagents was alternated with carrier fluid that optionally contained a flow marker. A 60 sec PCR cycle time was used including 10 sec at 95° C., 10 sec at 55° C. and 20 sec at 72° C. per cycle. The flow rate was approximately 1 mm per min with continuous flow in the microchannels during the experiment. The real-time PCR system used in this experiment included an LED array with a 470 nm peak and a 630 nm peak an excitation filter and a dual bandpass interference filter. The detector conditions were as follows: detector: CMOS 12.8 Mpixel; lens: 50 mm f/1.4; magnification: approximately 1:1; emission filter: interference filter with passbands of 510-565 nm and 660-710 nm; ISO sensitivity: 3200. Simultaneous multi-color image acquisition was performed during the 72° C. extension phase. SYBR Green dye was used to detect amplified product, and AlexaFluor 647 red dye was optionally used as a flow marker.

Figure 8A:
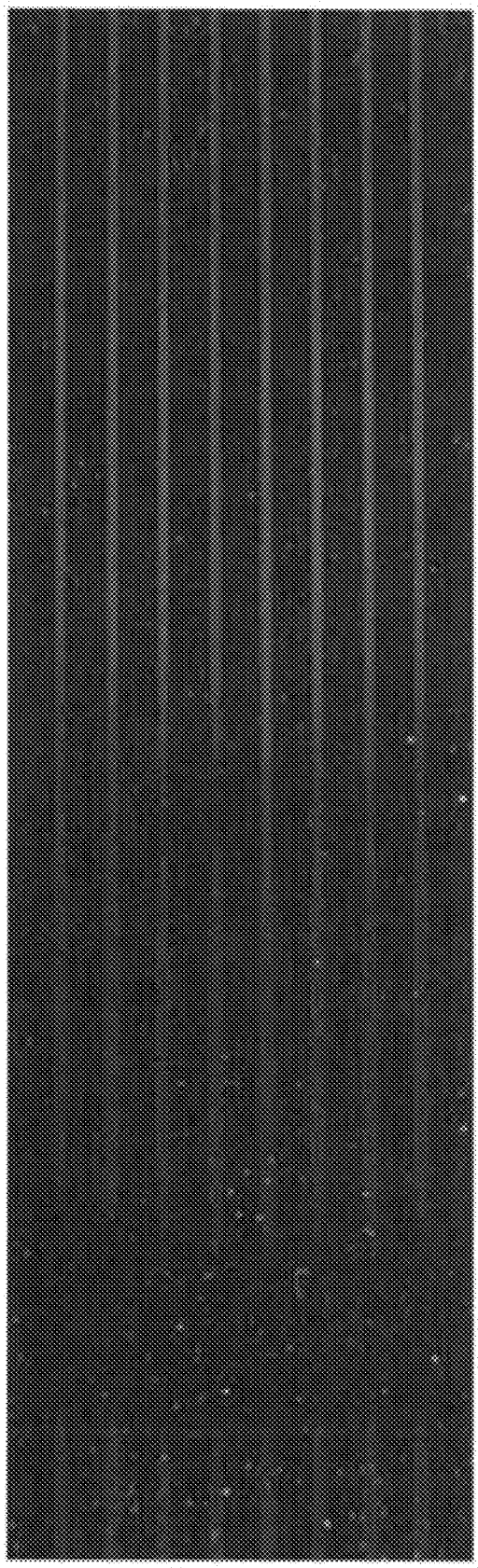
FIG. 8A is an image of a fluorescent signal showing the growth of PCR products in microfluidic channels under flow conditions.
Figure 8B:
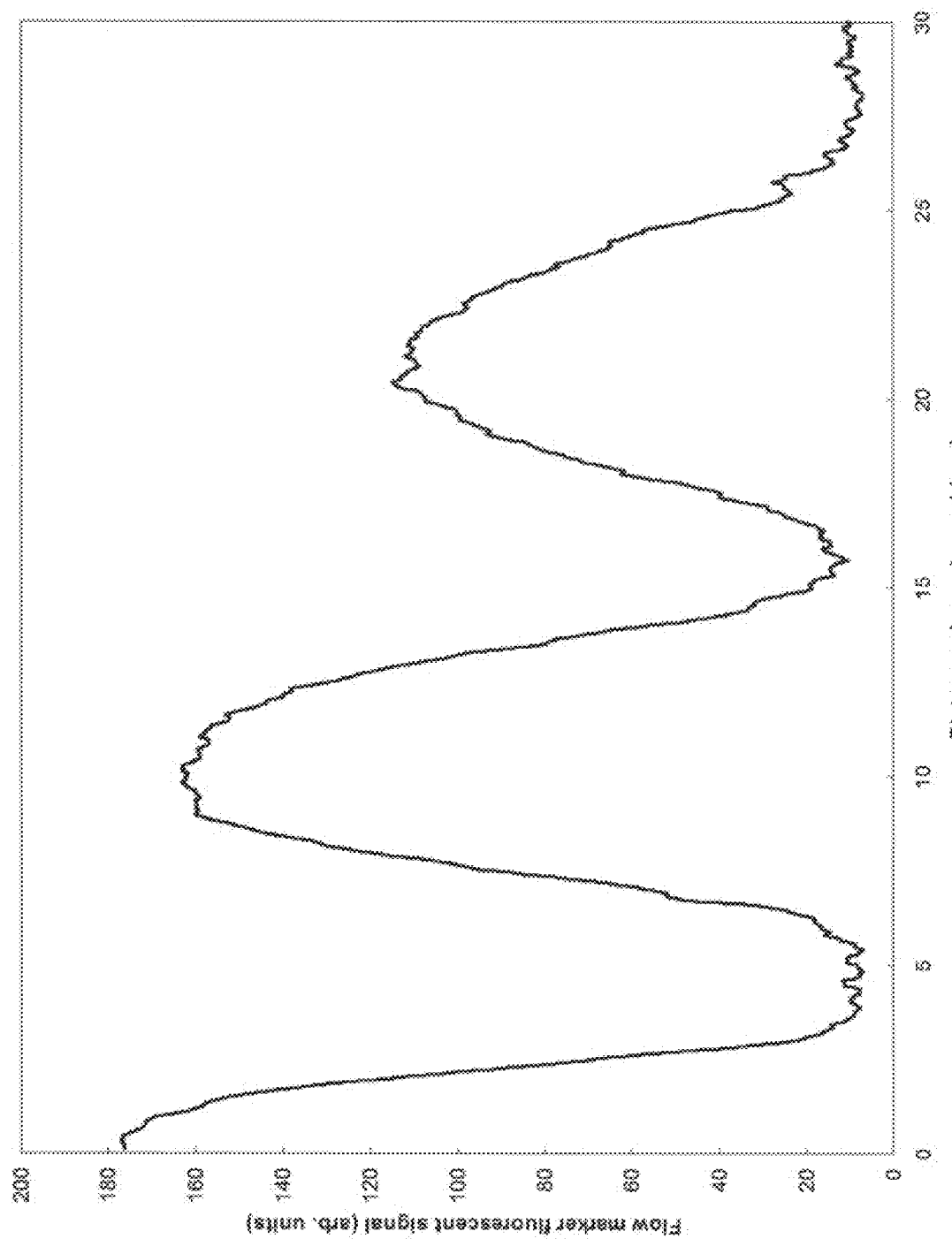
FIG. 8B is a plot of the intensity of the marker along a microchannel from FIG. 8A.

The results of this experiment are shown in FIGS. 8A-8B and FIGS. 9A-9B. FIG. 8A shows a 30 mm long section of the channels under continuous-flow PCR conditions. Red flow markers consisting of Alexa Fluor 647 dye boluses are visible. The green light, noticeable only at the downstream end of the channel on the right, is from SYBR Green I dye indicating the presence of amplified DNA. FIG. 8B shows a plot of the intensity of the red signal along microchannel 2 (second from the top) from FIG. 8A. Diffusion and dispersion cause these dye marker boluses to spread as they move down the channel, resulting in broader and shorter signal peaks downstream. Nevertheless, these effects are weak and the boluses retain sufficient distinctness so that they can be used to measure the flow speed.

Figure 9A:
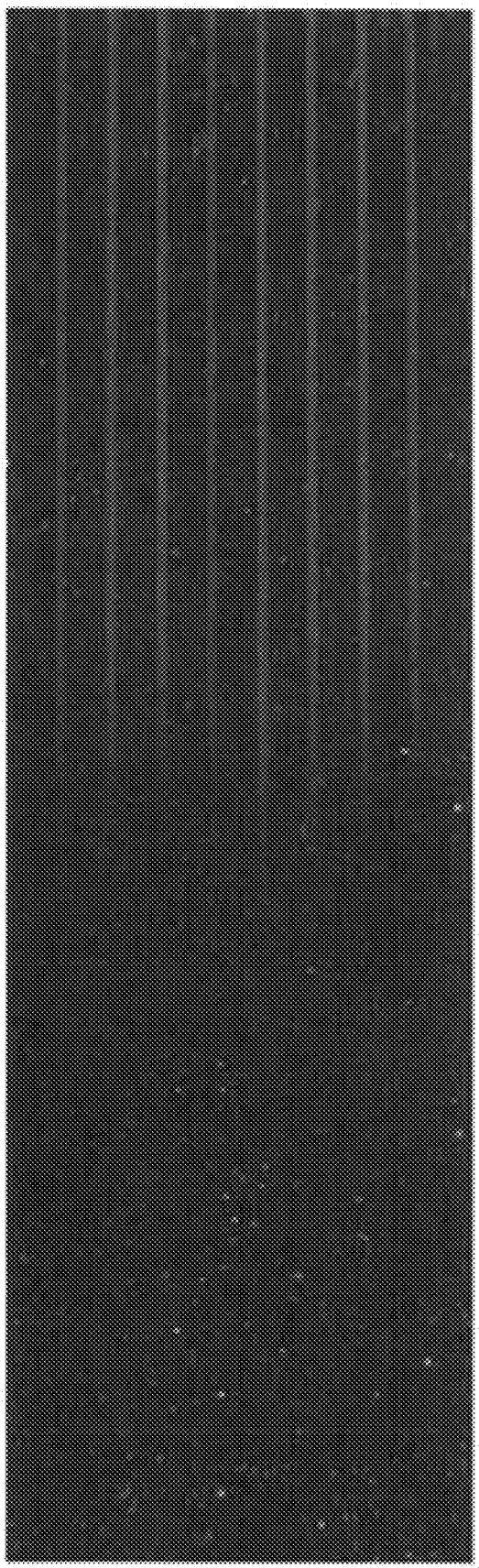
FIG. 9A is an image of a fluorescent signal showing the growth of PCR products in microfluidic channels under flow conditions.
Figure 9B:
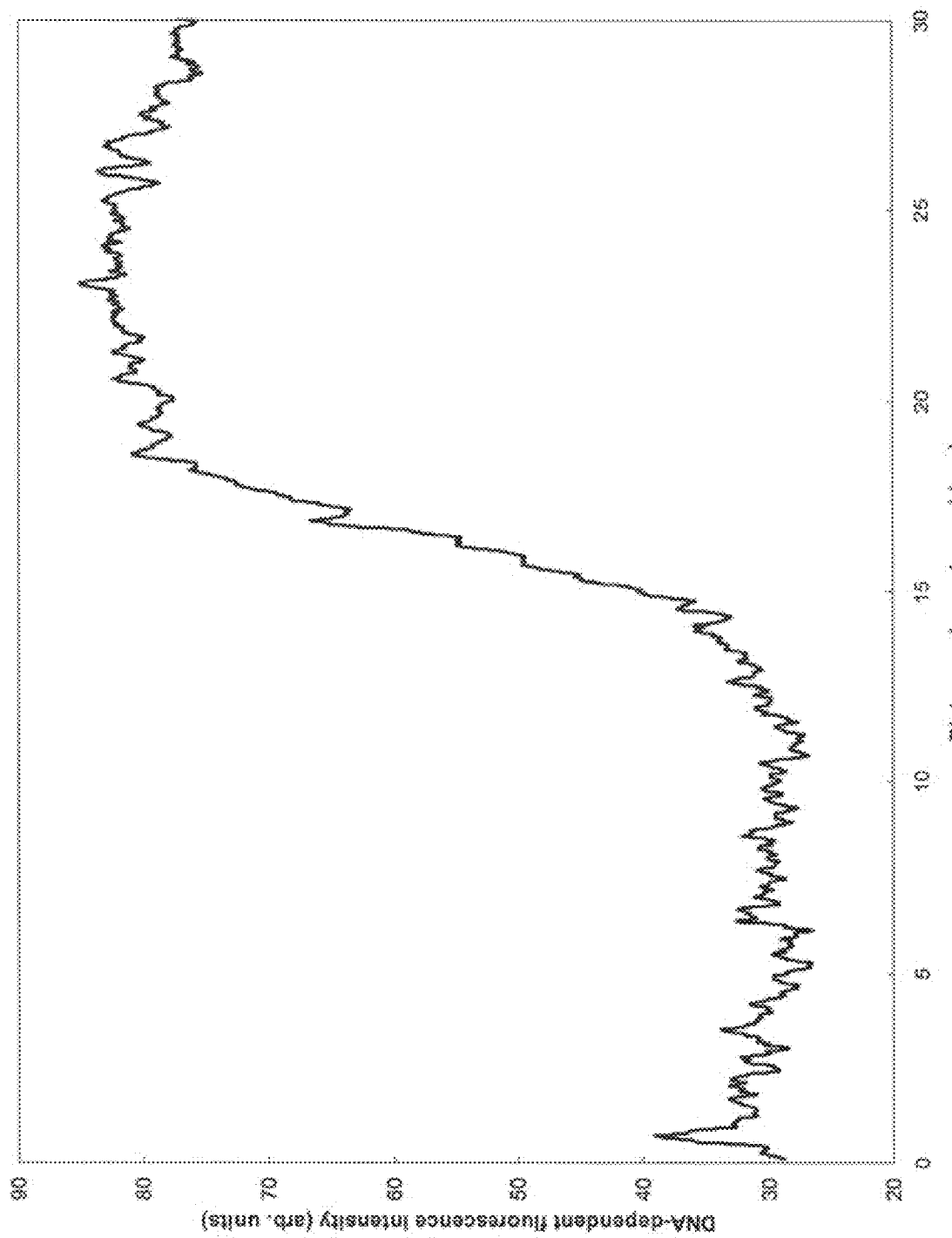
FIG. 9B is a plot of the intensity of the green signal along a microchannel from FIG. 9A.

FIG. 9A shows a 30 mm long section of the channels under continuous-flow PCR conditions. The green light is from SYBR Green dye fluorescence acquired during the extension phase and indicates the presence of amplified DNA. In this case, no separate flow markers were injected into the channels. FIG. 9B shows a plot of the intensity of the green signal along microchannel 2 (second from the top) from FIG. 9A. Toward the upstream end of the channel, where sample elements have experienced few PCR temperature cycles, the measured intensity is dominated by background scattering. Going downstream, the signal rises steeply and then saturates. This sigmoidal shape of signal versus position is similar to the shape of signal amplitude versus cycle number seen in conventional real-time PCR systems. These results show real-time detection of PCR amplification under continuous flow conditions.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A system for performing real-time PCR in a microfluidic device, said system comprising:
    a microfluidic device comprising at least one channel configured to contain at least one test solution containing real-time PCR reagents and at least one carrier fluid;
    a thermal transfer element integral with or proximal to the microfluidic device, said thermal transfer element configured to thermocycle the test solution along the length of a defined section of the at least one channel, wherein the defined section of the channel has a uniform temperature at any one time during temperature cycles for performing real-time PCR in the test solution within said defined section;
    a source of illumination integral with or proximal to the microfluidic device and configured to illuminate the at least one channel; and
    a detector integral with or proximal to the microfluidic device, said detector configured to detect a fluorescent signal at a plurality of locations along said defined section of said at least one channel.

2. The system of claim 1, further comprising a software system that measures an average flow speed of the test solution in the channel.

3. The system of claim 2, wherein said software system measures the average flow speed of the test solution by comparing sequential images of the fluorescent signal in the channel.

4. The system of claim 2, wherein said software system measures the average flow speed of the test solution by comparing sequential images of a marker in the channel.

5. The system of claim 4, wherein the marker is in the test solution.

6. The system of claim 4, wherein the marker is in the carrier fluid.

7. The system of claim 2, further comprising an element for controlling the flow speed of the at least one test solution continuously flowing in the at least one channel in response to the average flow speed measured by said computer system.

8. The system of claim 1, wherein the fluorescent signal is measured at least once during each PCR cycle.

9. The system of claim 1, wherein the detector is configured to detect a signal from amplification products and a signal from a marker at a plurality of locations along said defined section of said at least one channel.

10. The system of claim 9, wherein the detector is configured to independently detect signals from the amplified product and the marker.

11. The system of claim 1, wherein the at least one channel comprises a plurality of channels.

12. The system of claim 1, wherein the at least one test solution comprises a plurality of test solutions.

13. The system of claim 1, wherein the at least one carrier fluid comprises a plurality of carrier fluids.

14. The system of claim 1, further comprising a sensor to detect the temperature of the thermal transfer element and to provide feedback information for controlling the temperature cycles.

15. The system of claim 9, further comprising means for analyzing the amplified product.

* * * * *